(12) United States Patent
Faulhaber

(10) Patent No.: US 11,896,493 B2
(45) Date of Patent: *Feb. 13, 2024

(54) EXPANDABLE INTERVERTEBRAL SPACER

(71) Applicant: GLOBUS MEDICAL, INC., Audubon, PA (US)

(72) Inventor: Kurt Faulhaber, Renton, WA (US)

(73) Assignee: Globus Medical, Inc, Audubon, PA (US)

( * ) Notice: Subject to any disclaimer, the term of this patent is extended or adjusted under 35 U.S.C. 154(b) by 133 days.

This patent is subject to a terminal disclaimer.

(21) Appl. No.: 17/365,219

(22) Filed: Jul. 1, 2021

(65) Prior Publication Data
US 2021/0322182 A1   Oct. 21, 2021

Related U.S. Application Data

(60) Continuation of application No. 16/453,038, filed on Jun. 26, 2019, now Pat. No. 11,076,966, which is a
(Continued)

(51) Int. Cl.
*A61F 2/44* (2006.01)
*A61F 2/46* (2006.01)
(Continued)

(52) U.S. Cl.
CPC ............ *A61F 2/4425* (2013.01); *A61F 2/447* (2013.01); *A61F 2/4455* (2013.01); *A61F 2/4611* (2013.01); *A61B 17/8042* (2013.01); *A61B 17/8852* (2013.01); *A61B 2017/564* (2013.01); *A61F 2002/3081* (2013.01); *A61F 2002/30405* (2013.01); *A61F 2002/30482* (2013.01); *A61F 2002/30507* (2013.01); *A61F 2002/30515* (2013.01); *A61F 2002/30556* (2013.01); *A61F 2002/30578* (2013.01); *A61F 2002/30593* (2013.01); *A61F 2002/30836* (2013.01);
(Continued)

(58) Field of Classification Search
CPC ...... A61F 2/4425; A61F 2/4455; A61F 2/447; A61F 2002/443; A61F 2/4611
See application file for complete search history.

(56) References Cited

U.S. PATENT DOCUMENTS

| | | |
|---|---|---|
| 4,349,921 A | 9/1982 | Kuntz |
| 4,599,086 A | 7/1986 | Doty |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Anu Ramana

(57) ABSTRACT

A spacer for separating bones of a joint, the spacer includes a first endplate configured to engage a first bone of the joint; a second endplate configured to engage a second bone of the joint; and an actuation subassembly comprising a drive nut, a drive screw coupled to the drive nut, and a cam frame coupled to the drive screw, wherein the cam frame is disposed between the first endplate and the second endplate, wherein the cam frame comprises a proximal frame end, a distal frame end, and lateral frame sides, wherein cams disposed on the lateral frame sides selectively engage at least one of the first endplate or the second endplate.

12 Claims, 21 Drawing Sheets

Related U.S. Application Data division of application No. 14/970,598, filed on Dec. 16, 2015, now Pat. No. 10,369,004.

(51) Int. Cl.
  *A61F 2/30* (2006.01)
  *A61B 17/80* (2006.01)
  *A61B 17/88* (2006.01)
  *A61B 17/56* (2006.01)

(52) U.S. Cl.
  CPC ............ *A61F 2220/0016* (2013.01); *A61F 2230/0082* (2013.01); *A61F 2250/0009* (2013.01); *A61F 2250/0065* (2013.01)

(56) References Cited

U.S. PATENT DOCUMENTS

| | | |
|---|---|---|
| 4,863,476 A | 9/1989 | Sheppherd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim et al. |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 * | 1/2001 | Biedermann ............ A61F 2/447 623/17.11 |
| 6,258,125 B1 | 7/2001 | Paul et al. |
| 6,554,863 B2 | 4/2003 | Paul et al. |
| 6,558,423 B1 | 5/2003 | Michelson |
| 6,562,074 B2 | 5/2003 | Gerbec et al. |
| 6,576,016 B1 | 6/2003 | Hochshuler et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 * | 1/2009 | Aebi ............ A61F 2/4425 623/17.13 |
| 7,547,325 B2 | 6/2009 | Biedermann |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,105,382 B2 | 1/2012 | Olmos et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | JImenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | JImenez et al. |
| 9,532,883 B2 | 1/2017 | McLuen et al. |
| 9,622,878 B2 | 4/2017 | Grotz |
| 2002/0045945 A1 * | 4/2002 | Liu ............ A61F 2/446 623/17.16 |
| 2002/0068976 A1 | 6/2002 | Jackson |
| 2002/0068977 A1 | 6/2002 | Jackson |
| 2003/0176926 A1 | 9/2003 | Boehm et al. |
| 2004/0030387 A1 | 2/2004 | Landry et al. |
| 2004/0049271 A1 | 3/2004 | Biedermann et al. |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0113916 A1 | 5/2005 | Branch |
| 2005/0149188 A1 | 7/2005 | Cook et al. |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0250168 A1 | 10/2007 | Lechmann et al. |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |

(56) References Cited

U.S. PATENT DOCUMENTS

| | | |
|---|---|---|
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barriero et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0185291 A1 | 7/2010 | Jimenez |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0222816 A1 | 9/2010 | Gabelberger et al. |
| 2010/0222884 A1 | 9/2010 | Greenhalgh |
| 2010/0234952 A1 | 9/2010 | Peterman |
| 2010/0249933 A1 | 9/2010 | Trieu |
| 2010/0280622 A1 | 11/2010 | Mckinley |
| 2010/0286779 A1 | 11/2010 | Thibodeau |
| 2010/0286780 A1 | 11/2010 | Dryer |
| 2010/0286783 A1 | 11/2010 | Lechmann et al. |
| 2010/0292796 A1 | 11/2010 | Greenhalgh et al. |
| 2010/0305705 A1 | 12/2010 | Butler |
| 2010/0331981 A1 | 12/2010 | Mohammed |
| 2010/0331985 A1 | 12/2010 | Gordon |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0184522 A1 | 7/2011 | Melkent et al. |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 | 12/2000 |
| FR | 2794968 A1 | 12/2000 |
| FR | 2874814 A1 | 3/2006 |
| JP | 2000-513263 | 10/2000 |
| JP | 2000-513263 A | 10/2000 |
| JP | 2000513263 A | 10/2000 |
| JP | 2013508031 A | 3/2013 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 199942062 A1 | 8/1999 |
| WO | 1999042062 A1 | 8/1999 |
| WO | 199966867 A1 | 12/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | WO2006045094 A2 | 4/2006 |
| WO | 2006047587 A2 | 5/2006 |
| WO | 2006113080 A2 | 10/2006 |
| WO | WO2006113080 A2 | 10/2006 |
| WO | 2008044057 A1 | 4/2008 |
| WO | WO2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |

* cited by examiner

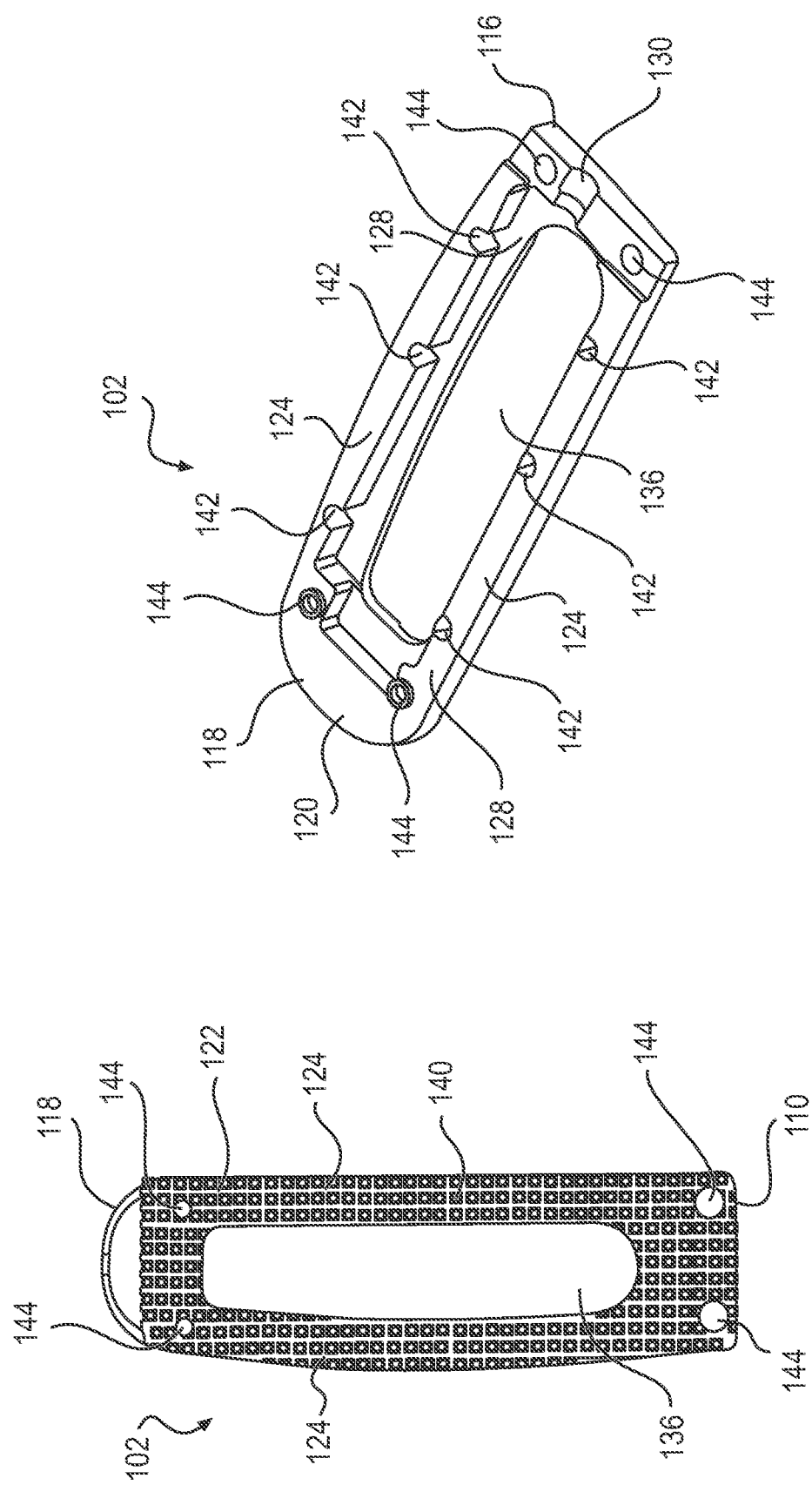

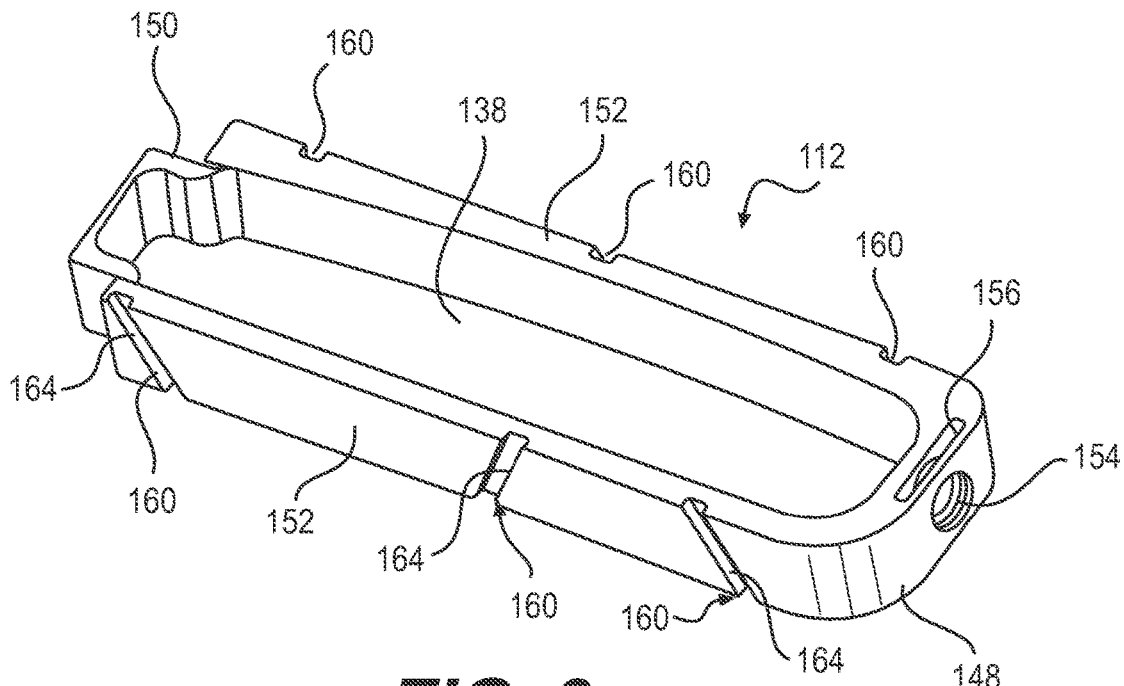
FIG. 6
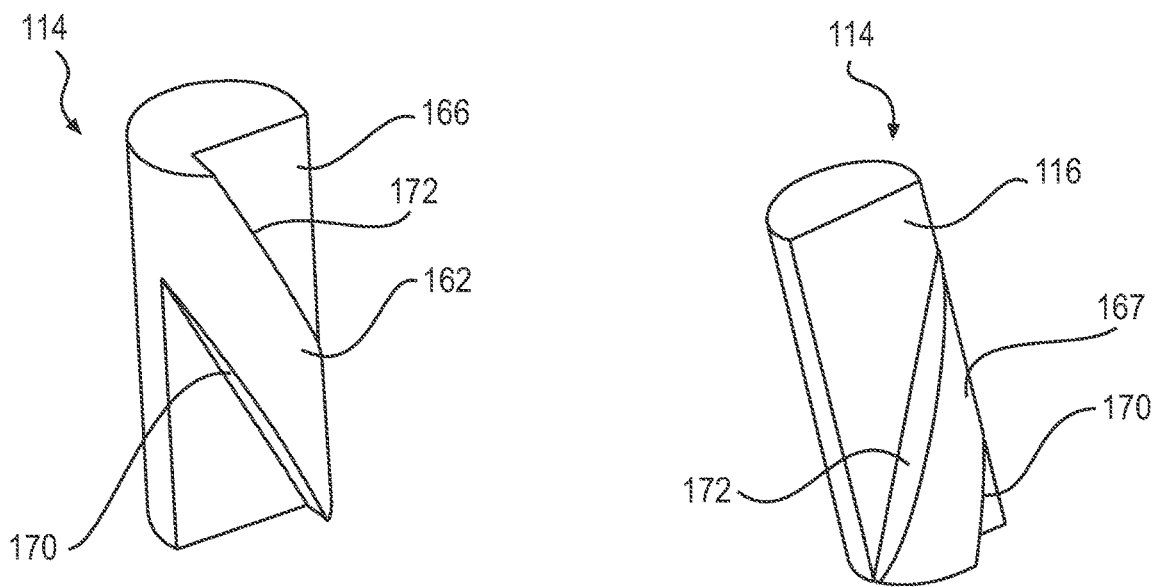
FIG. 7
FIG. 8

EXPANDABLE INTERVERTEBRAL SPACER

CROSS REFERENCE TO RELATED APPLICATIONS

This application is a continuation of U.S. patent application Ser. No. 16/453,038, filed on Jun. 26, 2109, which is a divisional of U.S. patent application Ser. No. 14/970,598, filed Dec. 16, 2015, 2015, which is incorporated by reference herein in its entirety for all purposes.

FIELD OF THE INVENTION

This invention relates to stabilizing adjacent vertebrae of the spine by inserting an intervertebral spacer, and more particularly an intervertebral spacer that is adjustable in height.

BACKGROUND

The vertebral or spinal column (spine, backbone) is a flexible assembly of vertebrae stacked on top of each other extending from the skull to the pelvic bone which acts to support the axial skeleton and to protect the spinal cord and nerves. The vertebrae are anatomically organized into four generalized body regions identified as cervical, thoracic, lumbar, and sacral; the cervical region including the top of the spine beginning in the skull, the thoracic region spanning the torso, the lumbar region spanning the lower back, and the sacral region including the base of the spine ending with connection to the pelvic bone. With the exception of the first two cervical vertebrae, cushion-like discs separate adjacent vertebrae, i.e. intervertebral discs.

The stability of the vertebral column during compression and movement is maintained by the intervertebral discs. Each disc includes a gel-like center surrounded by a fibrous ring. The gel-like center, i.e. nucleus pulposus, provides strength such that the disc can absorb and distribute external loads and contains a mixture of type II-collagen dispersed in a proteoglycan matrix. The fibrous ring, or annulus fibrosus, provides stability during motion and contains laminated rings of type-I collagen. Thus, the annulus fibrosis and the nucleus pulposus are interdependent, as the annulus fibrosis contains the nucleus pulposus in place and the nucleus pulposus aligns the annulus fibrosus to accept and distribute external loads. The integrity of the composition and structure of the intervertebral disc is necessary to maintain normal functioning of the intervertebral disc.

Many factors can adversely alter the composition and structure of the intervertebral disc, such as normal physiological aging, mechanical injury/trauma, and/or disease, resulting in impairment or loss of disc function. For example, the content of proteoglycan n the nucleus pulposus declines with age, thus, it follows that the ability of the nucleus pulposus to absorb water concurrently declines. Therefore, in normal aging the disc progressively dehydrates, resulting in a decrease in disc height and possible de-lamination of the annulus fibrosus. Mechanical injury can tear the annulus fibrosis allowing the gel-like material of the nucleus pulposus to extrude into the spinal canal and compress neural elements. Growth of a spinal tumor can impinge upon the vertebrae and/or disc potentially compressing nerves.

Bones of the spine, and bony structures, generally, are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column, in particular, requires additional support in order to address such weaknesses. One technique for providing support is to insert a spacer between adjacent vertebrae.

SUMMARY

In accordance with an embodiment of the disclosure, a spacer for separating bone of a joint may be provided, wherein the spacer may comprise: a first endplate configured to engage a first bone of the joint; a second endplate configured to engage a second bone of the joint; and an actuation subassembly comprising a drive nut, a drive screw coupled to the drive nut, and a cam frame coupled to the drive screw, wherein the cam frame is disposed between the first endplate and the second endplate, wherein the cam frame comprises a proximal frame end, a distal frame end, and lateral frame sides, wherein cams disposed on the lateral frame sides selectively engage at least one of the first endplate or the second endplate.

In accordance with an embodiment of the disclosure, a method of separating bones of a joint may be provided, wherein the method may comprise inserting a spacer between bones of the joint; and translating a cam frame along a longitudinal axis of the spacer, wherein cams disposed on the cam frame engage at least one of a first endplate and/or a second endplate increasing a height of the spacer.

BRIEF DESCRIPTION OF THE DRAWINGS

These drawings illustrate certain aspects of some examples of the present invention, and should not be used to limit or define the invention.

FIGS. 4 and 5 illustrate an endplate of a spacer in accordance example embodiments;

FIG. 6 illustrates a cam frame of a spacer of in accordance with example embodiments;

FIGS. 7 and 8 illustrate cam pins in accordance with example embodiments.

DETAILED DESCRIPTION

Embodiments are directed to a spacer that may be inserted between two adjacent bony surfaces to facilitate separation of the bones, and if desired, to promote the fusion of bony surfaces. Although intended to be useful with any adjacent bony surface in which fusion is desired, the spacer may advantageously be applied to insertion between two adjacent vertebral bodies in any section of the spine, including the cervical, thoracic, lumbar, and sacral vertebral sections. Additionally, the spacer may be implanted through an anterior, anterolateral, posterior, posterolateral, lateral, or any other suitable approach. More than one spacer may be implanted within the body, for example between successive or separated vertebrae, between adjacent vertebrae. The use of multiple spacers is particularly advantageous for patients whose back pain is not limited to a localized area, or for patients whose localized damage has progressed to other areas of the spine.

The spacer and methods for its insertion can be used in a treatment protocol for any of a wide variety of conditions in a patient involving diseased or damaged bony structures. The patient can be a human being. Additionally, it is contemplated that the spacer may be useful in veterinary science for any animal having adjacent bony structures to be fused. The spacer can collapse, for example, to approximately one half of an expanded size. When in this collapsed configuration, the spacer can be inserted into a space through a small incision and narrow pathways, using appropriate minimally-invasive techniques, and can be positioned within the space between adjacent bones, and there expanded to a desired therapeutic height. The incision may be short, for example about one inch in length, which is smaller than the spacer in an expanded configuration. If the desired position and/or expansion are not achieved, the spacer can be collapsed, repositioned, and re-expanded in situ.

Although the spacer is exemplified herein for use in the spine, the spacer is contemplated for fusion of any bony structures. While the spacers are described herein using several varying embodiments, the spacers are not limited to these embodiments. An element of one embodiment may be used in another embodiment, or an embodiment may not include all described elements.

Figure 1:
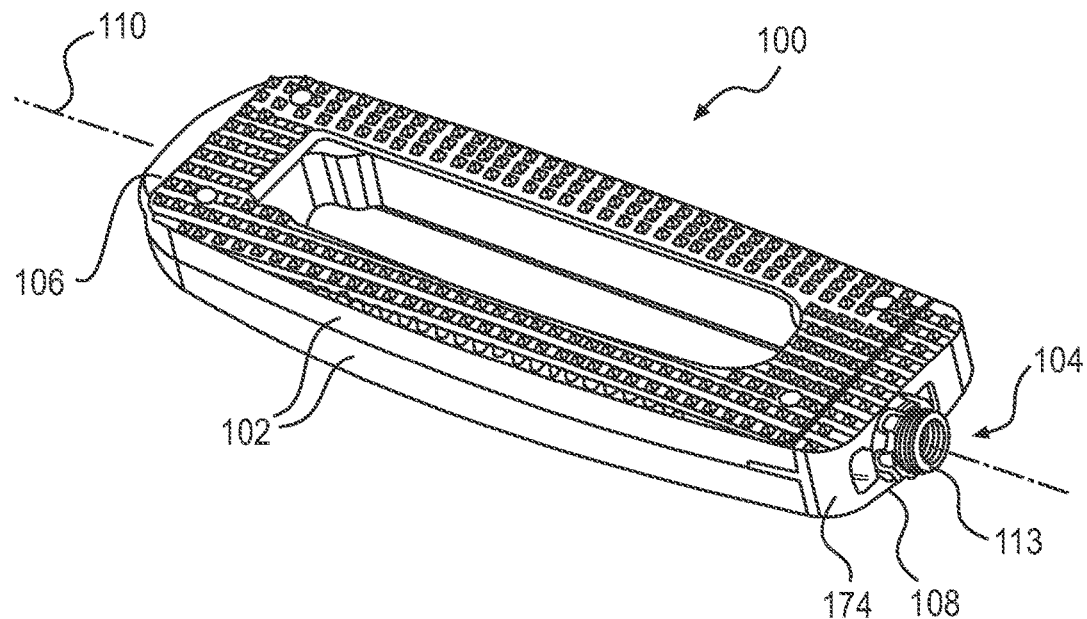
FIG. 1 is a perspective view of a spacer in a collapsed position in accordance with example embodiments.
Figure 2:
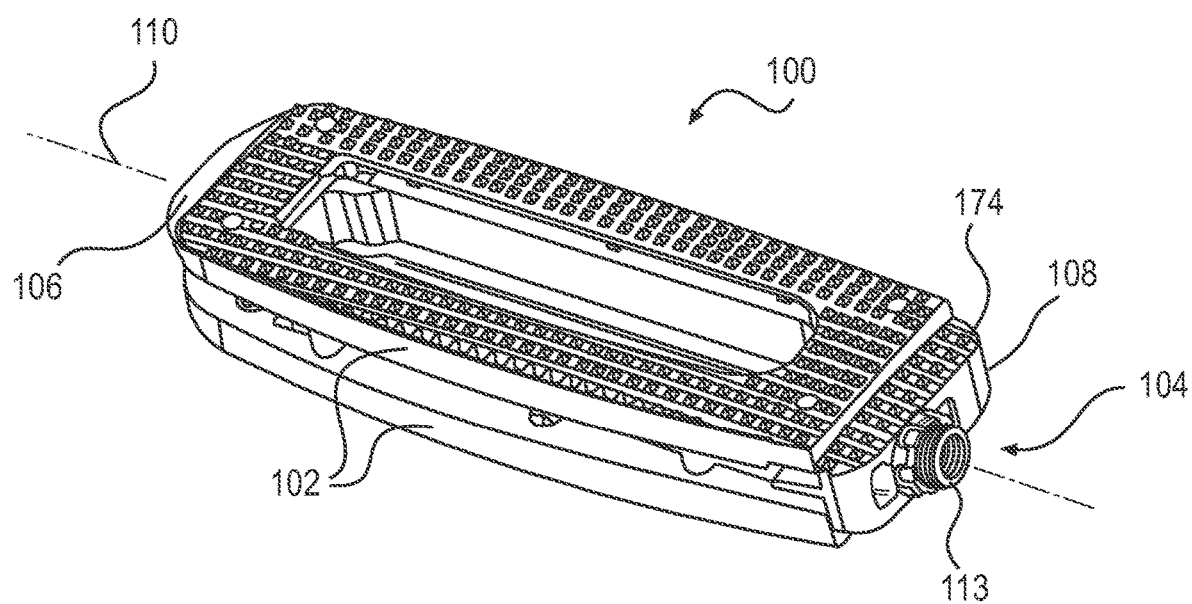
FIG. 2 is a perspective view of a spacer in an expanded position in accordance with example embodiments.
Figure 3:
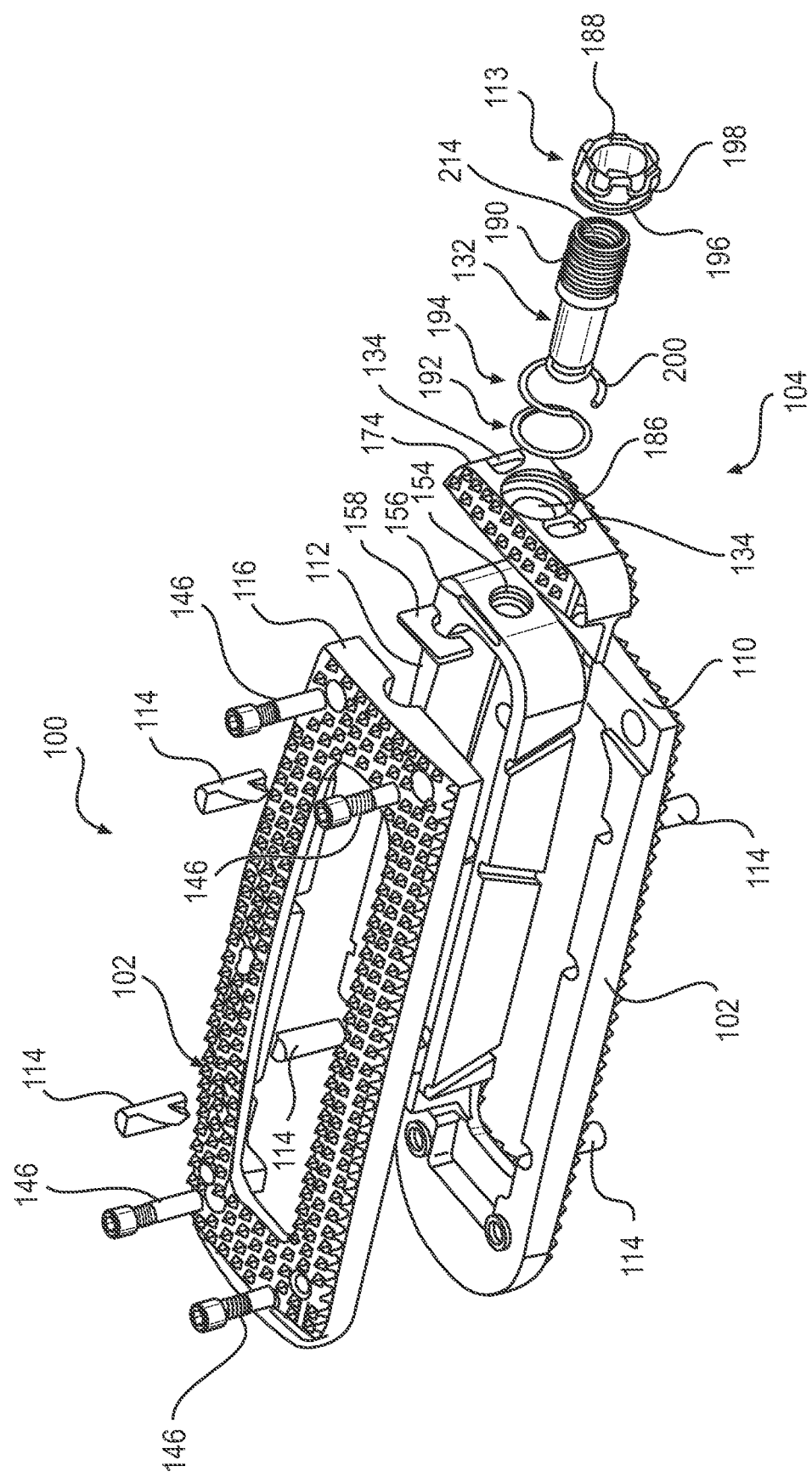
FIG. 3 is an exploded view of a spacer in accordance with example embodiments.

With reference now to FIGS. 1-3, embodiments of spacer 100 may comprise endplates 102 and actuation subassembly 104. In the embodiment shown, endplates 102 may be generally symmetrical, and spacer 100 can be implanted with either endplate 102 positioned superior with respect to the other. In other embodiments, they may be dissimilar, and a particular orientation may then be advantageous or necessary. While spacer 100 shown on FIGS. 1-3 may be implanted using a variety of approaches, spacer 100 may be particularly suitable for a lateral approach.

Spacer 100 forms a distal end 106 which may be inserted first into the body, and which can be tapered to facilitate insertion between body tissues. Spacer 100 also forms a proximal end 108, to which a spacer insertion device (e.g. 202 shown on FIGS. 12 and 13) may be connected. Spacer 100 may be inserted in a collapsed position, as shown on FIG. 1. Distal end 106 and proximal end 108 define a spacer longitudinal axis 110. The spacer 100 may be expanded, as shown on FIG. 2, after it has been inserted. To expand spacer 100, cam frame 112 (best seen on FIG. 3) may be displaced related to endplates 102. As the cam frame 112 translates along spacer longitudinal axis 110, cam frame 112 engages cam pins 114, driving them outward and, in turn, pushing endplates 102 relatively apart such that a height of spacer 100 may be increased. As will be discussed in more detail below, translation of cam frame 112 may be effected by rotation of drive nut 113.

Turning now to FIGS. 4 and 5, embodiments of endplates 102 will now be described. It should be understood that the endplates 102 may be symmetrical so the description may equally apply to either of endplates 102. Endplates 102 may have a plate proximal end 116 and a plate distal end 118. Nose 120 at plate distal end 118 may be tapered or otherwise formed to facilitate insertion into a desired location. As best seen on FIG. 4, endplates 102 may further comprise an outer facing surface 122 connecting plate proximal end 116 and plate distal end 118. As illustrated, endplates 102 may also comprise lateral sides 124. Endplates 102 may further comprise an inner facing surface 126. Inner facing surface 126 may have a recessed portion 128 in which cam frame 112 may be received. In the illustrated embodiment, endplates 102 may further comprise a cutout 130 for receiving drive screw 132 (e.g., shown on FIG. 3).

In some embodiments, endplates 102 may further comprise through openings 136. Through openings 136 may form an opening in endplates 102 that extends from outer facing surface 122 to inner facing surface 126. The through opening 136, in an exemplary embodiment, may be sized to receive bone graft or similar bone growth inducing material and further allow the bone graft or similar bone growth inducing material to be packed in a central opening 138 in cam frame 112 (best seen on FIG. 6).

With specific reference to FIG. 4, the outer facing surfaces 122 of endplates 102 may be flat and generally planar to allow the outer facing surfaces 122 to engage with the adjacent tissue (e.g., vertebral body). Alternatively, not shown, the outer facing surfaces 122 may be curved, convexly or concavely to allow, for a greater or lesser degree of engagement with the adjacent tissue, h is also contemplated that the outer facing surfaces 122 can be generally planar but include a generally straight ramped surface or a curved ramped surface. Where present, the ramped surface may allow for engagement with the adjacent tissue in a lordotic fashion. In the illustrated embodiment, the outer facing surfaces 122 comprise texturing 140, for example, to aid in gripping the adjacent tissue Although not limited to the following, the texturing can include teeth, ridges, friction increasing elements, keels, or gripping or purchasing projections.

As seen in FIGS. 6a and 6b, the endplates 102 may further include a plurality of holes 142. In some embodiments, holes may be blind holes that do not extend through outer facing surfaces 122. The holes 42 may be configured to receive cam pins 114, for example. The holes 142 may define a cam contact surface in which motion of the cam pins 114 is transferred to endplates 102. As illustrated, the holes 142 may be arranged in a row in each lateral side 124 of the endplates 102. In the illustrated embodiment, there are three holes 142 in each lateral side 124. However, it should be understood that the number and arrangement of holes 142 in endplates 102 may be selected as desired for a particular application. In addition, guide pin holes 144 may be also be disposed in at least one of the endplates 102. Guide pins 146 (e.g., shown on FIG. 3) may be disposed in fastener holes 144, for example, to guide expansion of endplates 102.

Endplates 102 may additionally, or alternatively, be resilient, so that they may conform to bony surfaces, forming a more stable support platform. Accordingly, endplates 102 can be fabricated from a polymeric material, a naturally resilient material, or a resilient metal, for example a shape memory alloy, or any other resilient biocompatible material of sufficient strength and durability for separating bones within the body.

Turning now to FIGS. 3 and 6, cam frame 112 will now be described in more detail with respect to particular embodiments. As illustrated, cam frame 112 may comprise proximal frame end 148, distal frame end 150, and lateral frame sides 152. Lateral frame sides 152 may extend from proximal frame end 148 to distal frame end 150. Proximal frame end 148, distal frame end 150, and lateral frame sides 152 may define central opening 138 in cam frame 112. Opening 154 may be formed in proximal frame end 148 through which drive screw 132 may be disposed. Retaining slots 156 may be formed in proximal frame end 148 that intersect opening 154. One or more screw retaining plates 158 may be inserted into retaining slots 156 to retain drive screw 132.

In some embodiments, cam slots 160 may be formed in lateral frame sides 152. As illustrated three cam slots 160 may be formed in each of lateral frame sides 152. However, it should be understood that more or less than three cam slots 160 may be used. The number of cam slots 160 generally may correspond to the number of cam pins 114. At least a portion of cam pins 114 may be disposed in a corresponding one of cam slots 160. By way of example, each of cam pins 114 may include a protuberance, such as ridge 162 (best seen on FIGS. 7 and 8). The ridge 162 may ride in cam slots 160. The cam slots 160 may include drive surfaces 164 that engage cam pins 114. The cam slots 160 may operate to change the direction of the linear movement of cam frame 112. For example, movement of the cam frame 112 along the spacer longitudinal axis 110 may be changed to movement of cam pins 114 in a direction generally transverse to spacer longitudinal axis 110. As the cam frame 112 is moved, for example, along the spacer longitudinal axis 110, the cam slots 160 may engage the cam pins 114 to drive the cam pins 114 against the endplates 102, pushing endplates 102 relatively apart such that a height of spacer 100 may be increased. Cam slots 160 may be arranged so that expansion may be achieved with advancement or withdrawal of cam frame 112 with movement of the cam frame 112 in the opposite direction causing the cam slots 160 to engage the cam pins 114 to drive the cam pins 114 into a collapsed position, thus collapsing the endplates 102. As illustrated, the cam slots 160 may be angled with respect to spacer longitudinal axis 110. As will be appreciated, the angle of cam slots 160 may be adjusted to modify expansion of endplates 102.

Turning now to FIG. 7, an example cam pin 114 is illustrated in more detail in accordance with embodiments of the present disclosure. In the illustrated embodiment, cam pin 114 may comprise an elongated body portion 166 and ridge 162. In operation, the cam pin 114 may engage one of endplates 102 driving it outward. As illustrated, ridge 162 may project from elongated body portion 166 and extend at an angle with respect to the elongated body portion 166. As previously described, ridge 162 may ride in cam slots 160 of cam frame 112. Ridge 162 may include a drive surface 170 and a return surface 172. Motion of cam frame 112 may be transferred to cam pin 114 through drive surface 170 as endplates 102 are being driven outward, while motion of cam frame 112 may be transferred to cam pins 114 through return surface 172 as endplates 102 are being retracted. FIG. 8 illustrates an alternative embodiment of a cam pin 114 in which drive surface 170 is disposed on an opposite side of ridge 162 from the embodiment shown on FIG. 8. The positioning of drive surface 170 with respect to return surface 172 may depend on the angle of the cam slot 160 into which the cam pin 114 may be disposed. Depending on the angle of cam slots 160, the cam pins 114 of FIGS. 7 and 8 may be used separately or in combination.

Figure 9:
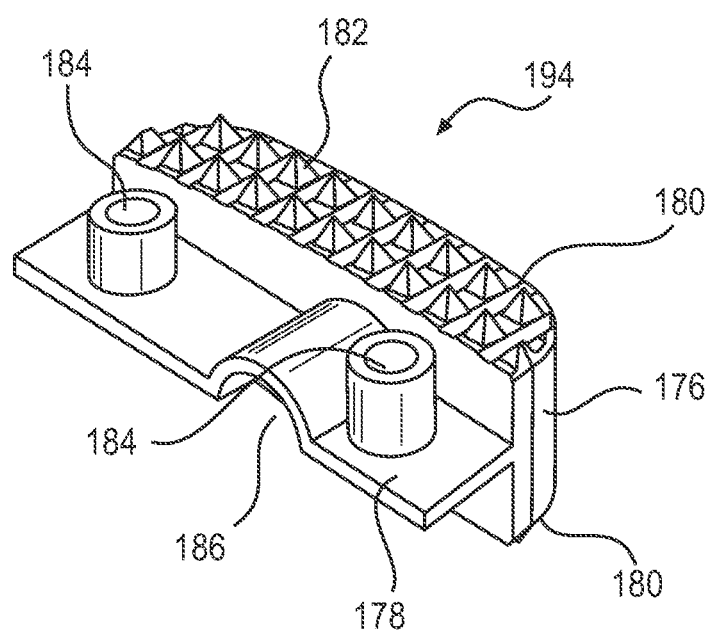
FIG. 9 illustrates a front plate in accordance with example embodiments.

Front plate 174 of spacer 100 is shown in more detail on FIGS. 3 and 9 in accordance with example embodiments. As best seen on FIG. 9, front plate 174 may include a plate body 176 and an extension 178. Front plate 174 may be arranged so that extension 178 extends from plate body 176 toward spacer distal end 106. Plate body 176 may also include outer facing surfaces 180. In the illustrated embodiment, the outer facing surfaces 180 comprise texturing 182, for example, to aid in gripping the adjacent tissue. Although not limited to the following, the texturing can include teeth, ridges, friction increasing elements, keels, or gripping or purchasing projections. In some embodiments, extension 178 may also include extension guide pin holes 184 for receiving guide pins 146. As best seen on FIG. 3, front plate 174 may be disposed plate proximal end 116 with extension 178 extending between endplates 102. Front plate 174 may be positioned so that guide pin holes 184 may align with guide pin holes 144 in endplates 102. Front plate 174 may further include a through bore 186, which may extend through front plate 174, for example, in a direction of spacer longitudinal axis 110. Plate body 176 may further comprise an insertion tool engagement 134, best seen on FIG. 3, which engages a corresponding engagement of spacer insertion device (e.g., 202 on FIGS. 12 and 13).

Figure 10:
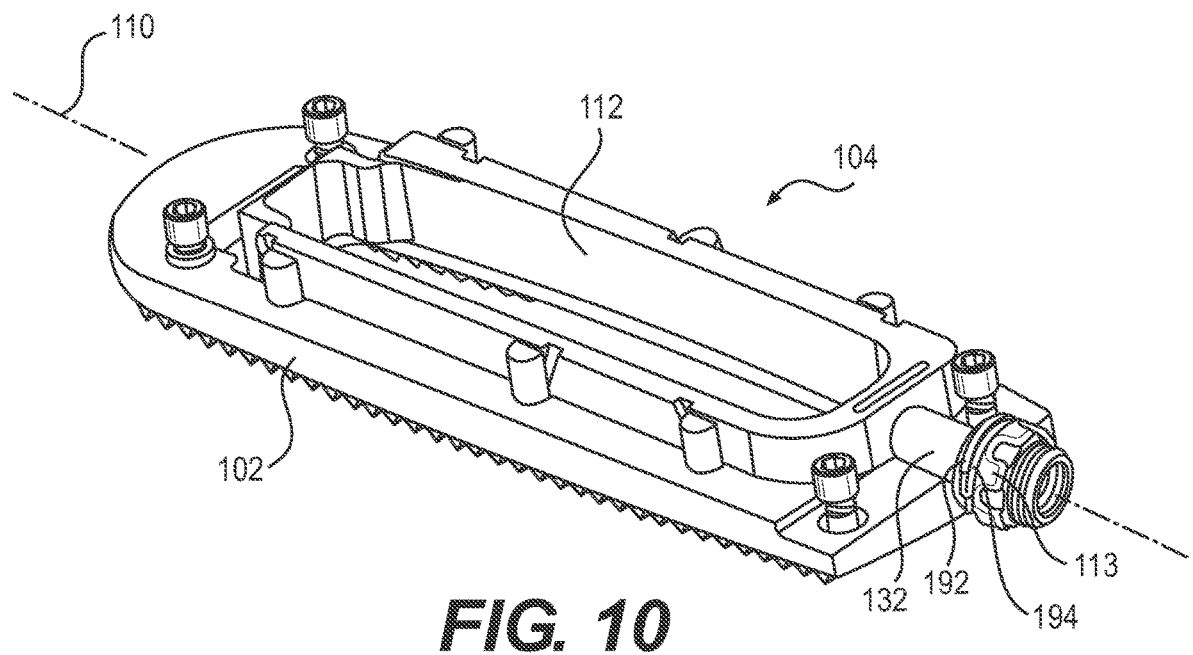
FIGS. 10 and 11 illustrate an actuation subassembly positioned with an endplate in accordance with example embodiments.
Figure 11:
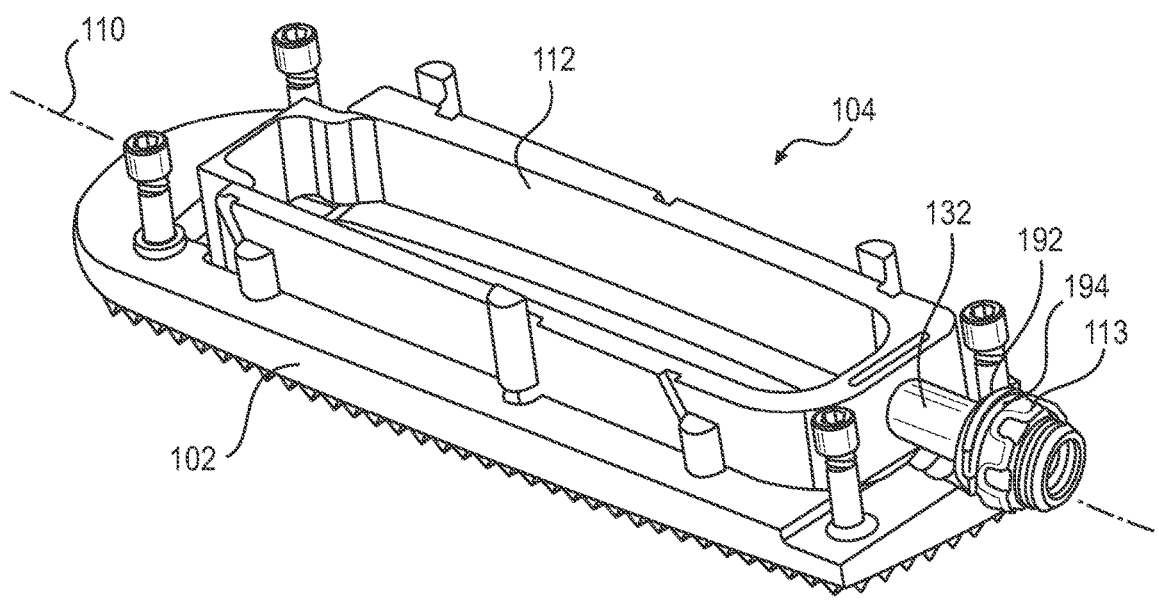

FIGS. 10 and 11 illustrate actuation subassembly 104 in accordance with embodiments of the present invention. Embodiments of actuation subassembly 104 will also described with additional reference to FIG. 3. Action subassembly 104 may extend between endplates 102. In the illustrated embodiments, one of the endplates 102 has been removed to better show actuation subassembly 104. FIG. 10 illustrates the actuation assembly 104 in a collapsed position, and FIG. 11 illustrates the actuation assembly 104 in an expanded position.

As illustrated, actuation subassembly 104 may comprise cam frame 112, drive screw 132, and drive nut 113. Cam frame 112 may be displaced relative to endplates 102 by rotation of drive nut 113 which in turn moves drive screw 132 and cam frame 112 along spacer longitudinal axis 110. In some embodiments, rotation of drive nut 113 may cause cam frame 112 to translate a path along spacer longitudinal axis 110. A spacer insertion device (e.g., 202 on FIGS. 12 and 13) may interact with drive nut 113 to cause rotation of drive nut 113 so that cam frame 112 may be advanced and/or withdrawn. As the cam frame 112 is advanced, the cam frame 112 may drive the cam pins 114 causing them to push endplates 102 from a collapsed position (e.g., shown on FIG. 10) to an expanded position (e.g., shown on FIG. 11).

Embodiments of drive nut 113 may also include a nut through bore 188, which may be threaded as best seen on FIG. 3. Drive screw 132 may include a threaded portion 190. Threaded portion 190 may threadingly engage nut through bore 188 so that drive nut 113 may be retained on drive screw 132. Embodiments may further include a first ring 192 and a second ring 194, which one or both may be in the form of a c-ring or other suitable device. In some embodiments, first ring 192 may be a washer and second ring 194 may be a c-ring. In some embodiments, first ring 192 and/or second ring 194 may be compressible. In some embodiments, first ring 192 and/or second ring 194 may be retained on corresponding grooves found on extension 196 from head portion 198 of drive nut 113. When assembled, first ring 192 may be disposed between endplates 102 and drive nut 113. In some embodiments, extension 196 of drive nut 113 may be secured in through bore 186 of front plate 174. For example, extension 196 may threadingly engage through bore 186. Second ring 194 may be disposed on extension 196 during insertion into through bore 186 of endplates 102 and then expand, thus securing drive nut 113 to front plate 174.

In some embodiments, drive screw 132 may be secured in drive nut 113 at one end and be secured to cam frame 112 at another end. Drive screw 132 may include a retainer groove 200, best seen on FIG. 3. As illustrated, retainer groove 200 may be disposed at an opposite end of drive screw 132 from threaded portion 190. Drive screw 132 may extend into opening 154 in cam frame 112. One or more screw retaining plates 158 may inserted into retaining slots 156 to engage drive screw 132. For example, screw retaining plates 158 may engage retainer groove 200 so that drive screw 132 may be retained in opening 154.

Figure 12:
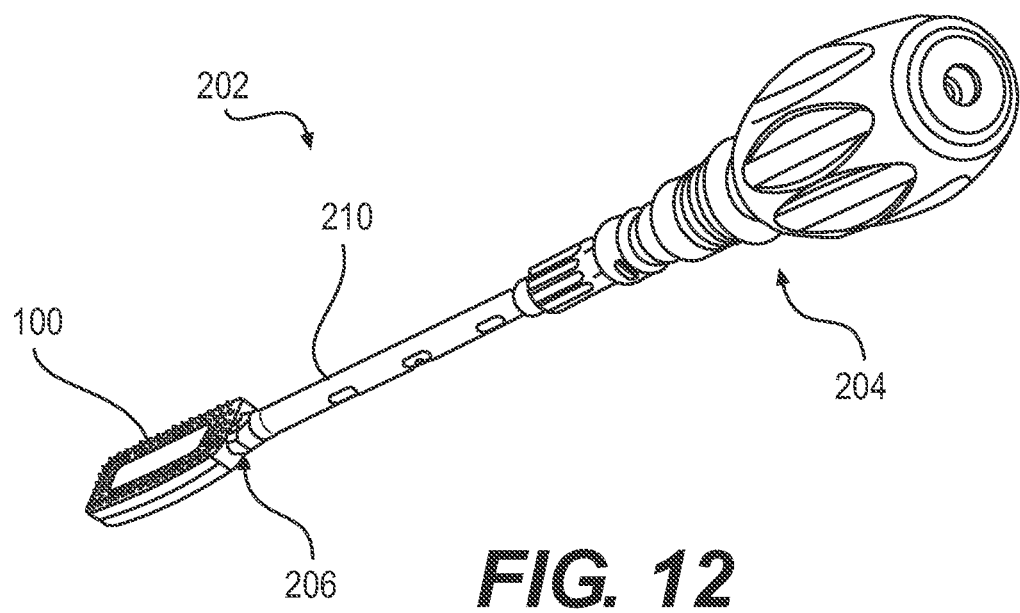
FIGS. 12 and 13 illustrate a spacer insertion device in accordance with example embodiments.
Figure 13:
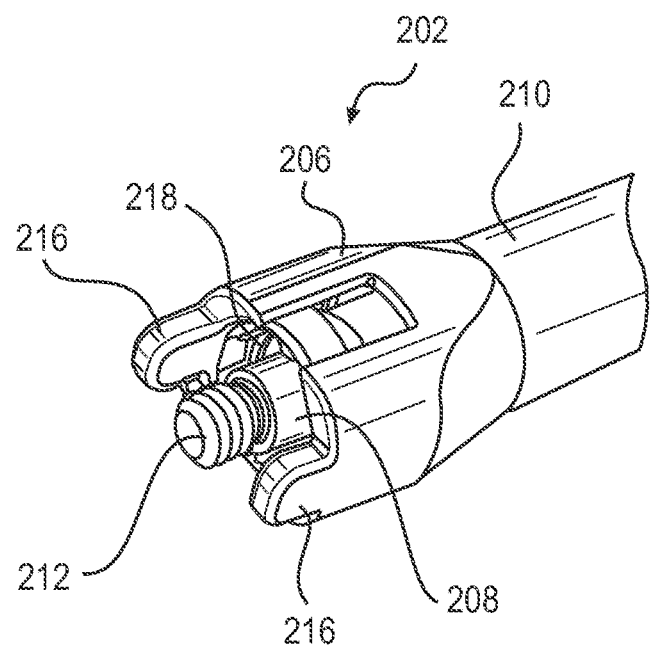
Figure 14:
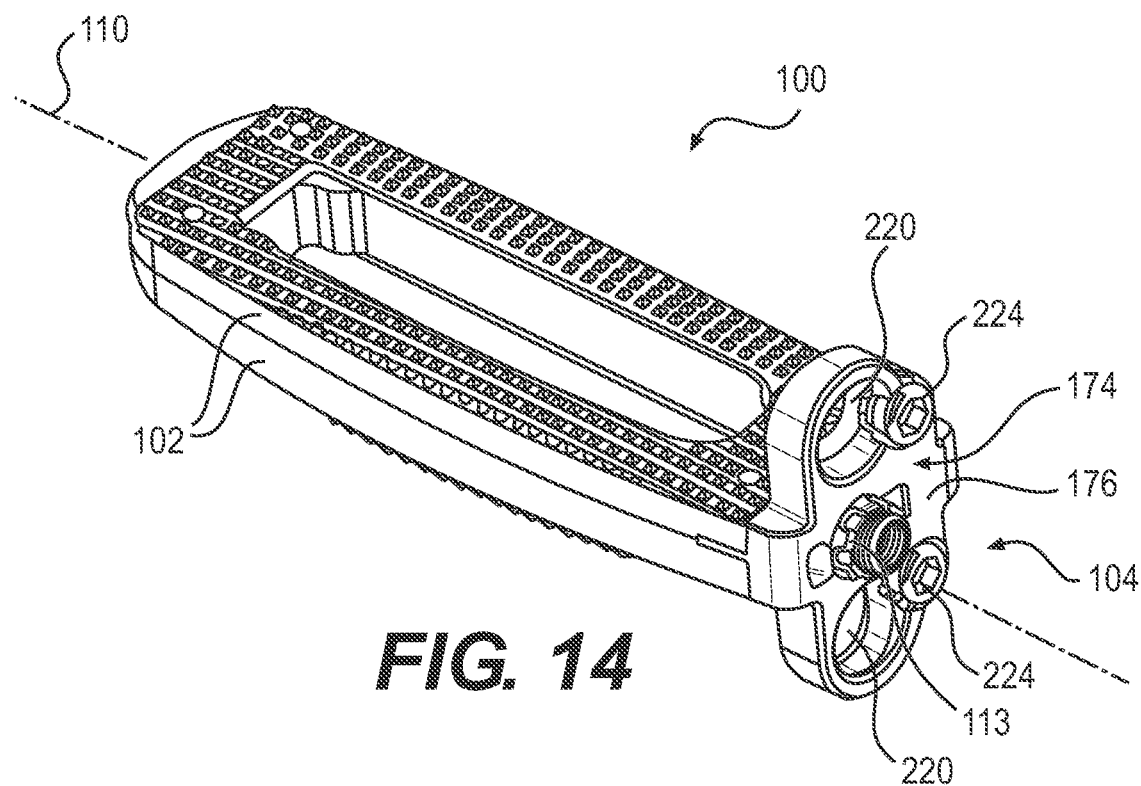
FIG. 14 is a perspective view of a spacer in a collapsed position in accordance with example embodiments.
Figure 15:
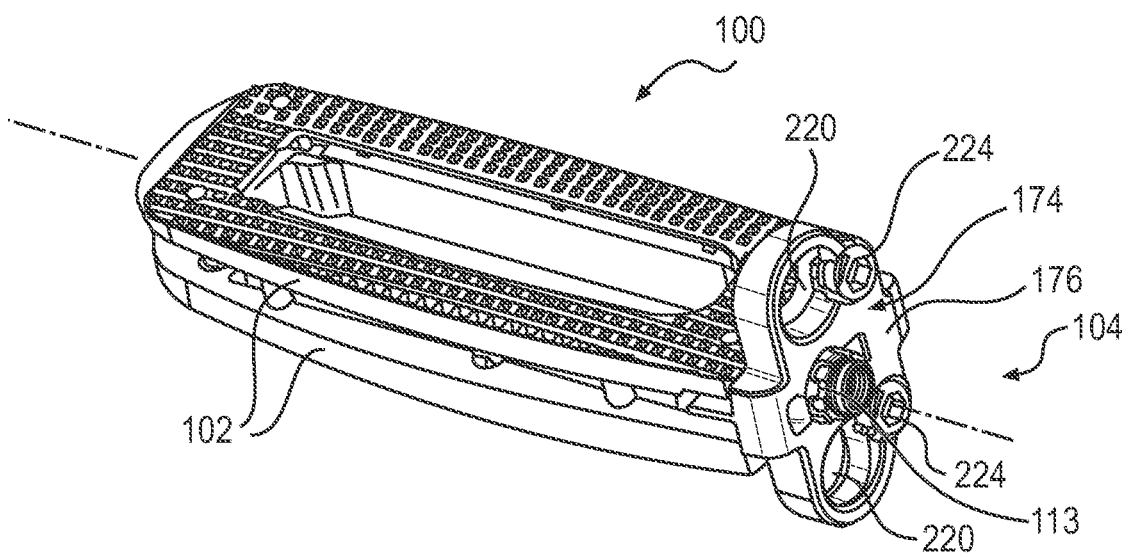
FIG. 15 is a perspective view of a spacer in an expanded position in accordance with example embodiments.
Figure 16:
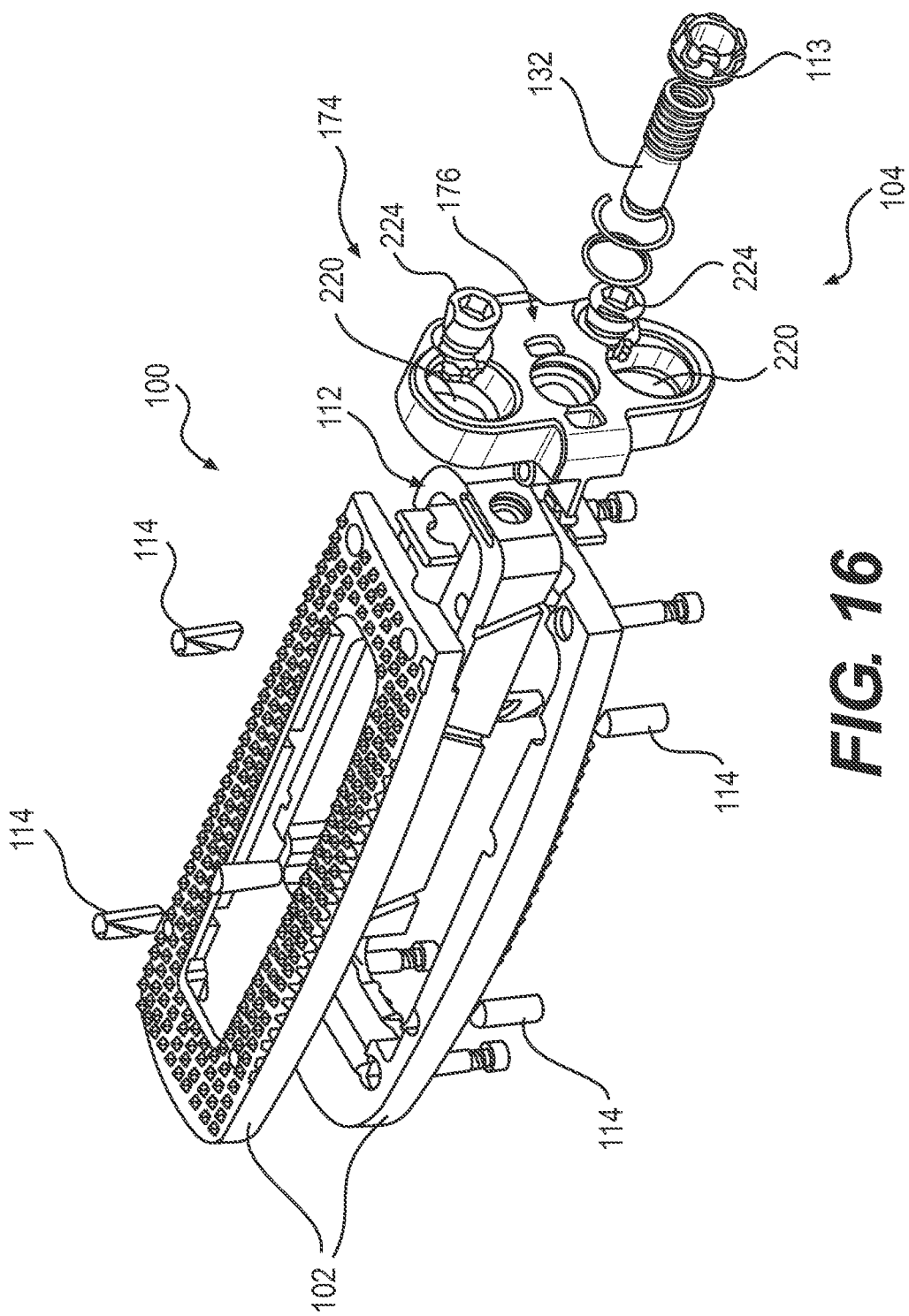
FIG. 16 is an exploded view of a spacer in accordance with example embodiments.
Figure 17:
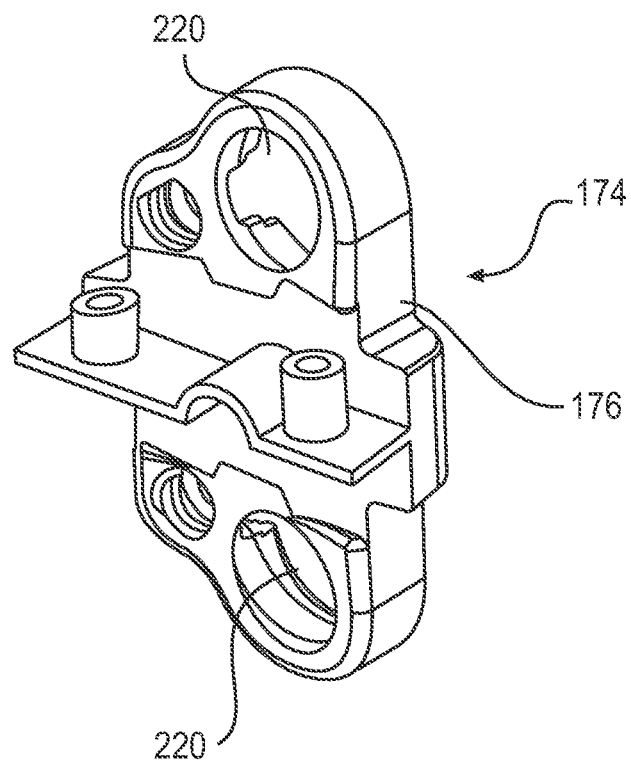
FIG. 17 illustrates a front plate of a spacer in accordance with example embodiments.
Figure 18:
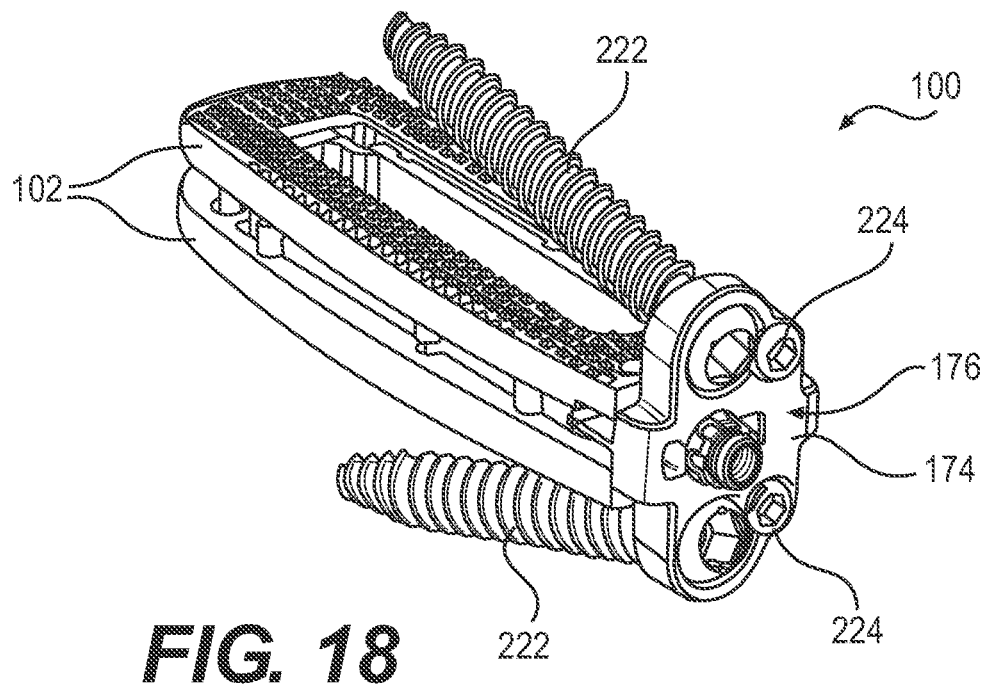
FIG. 18 illustrates a spacer in accordance with example embodiments.
Figure 19:
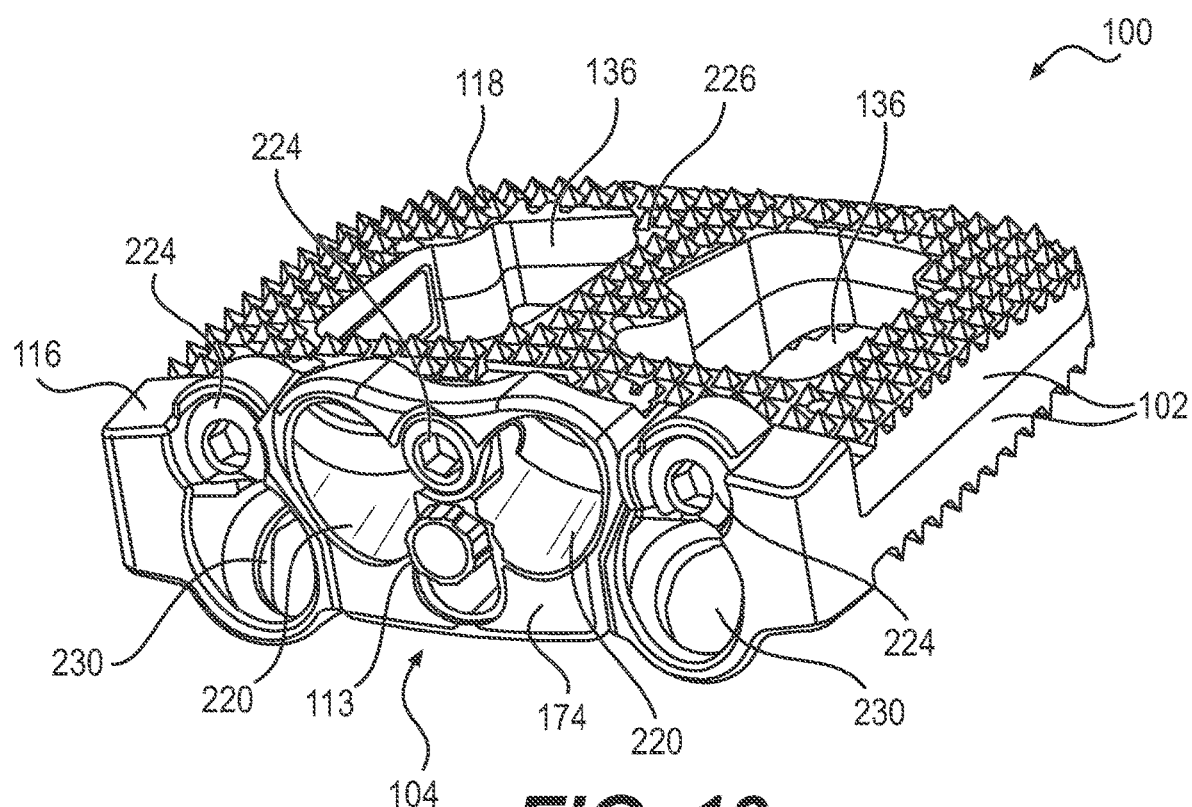
FIG. 19 is a perspective view of a spacer in a collapsed position in accordance with example embodiments.
Figure 20:
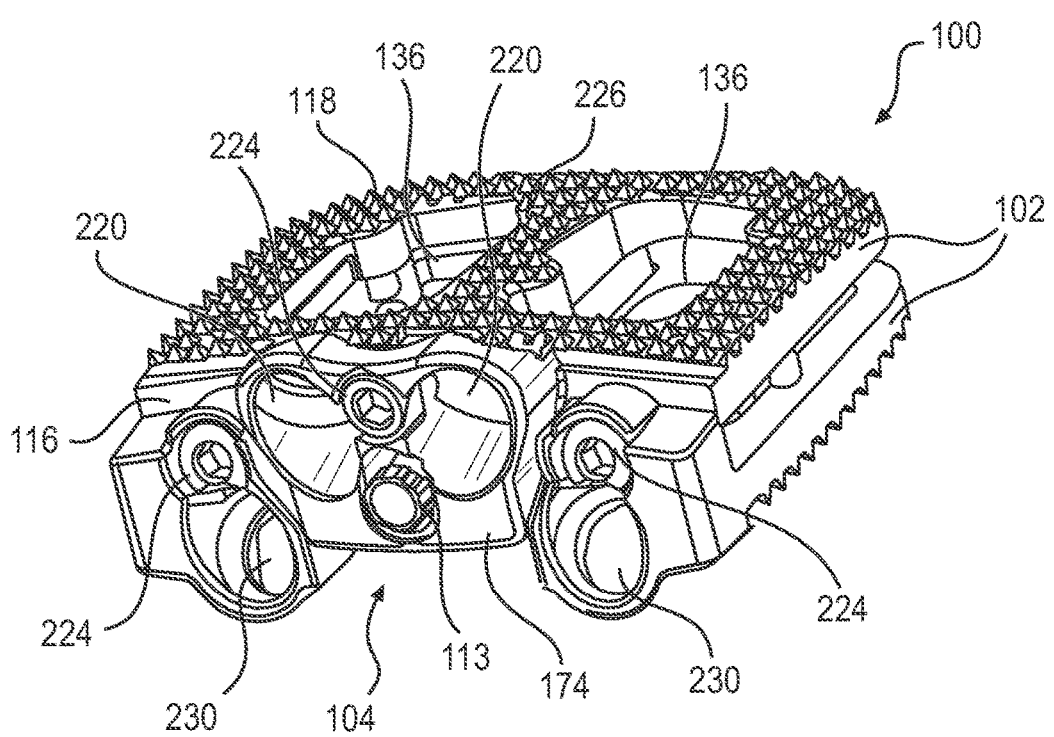
FIG. 20 is a perspective view of a spacer in an expanded position in accordance with example embodiments.
Figure 21:
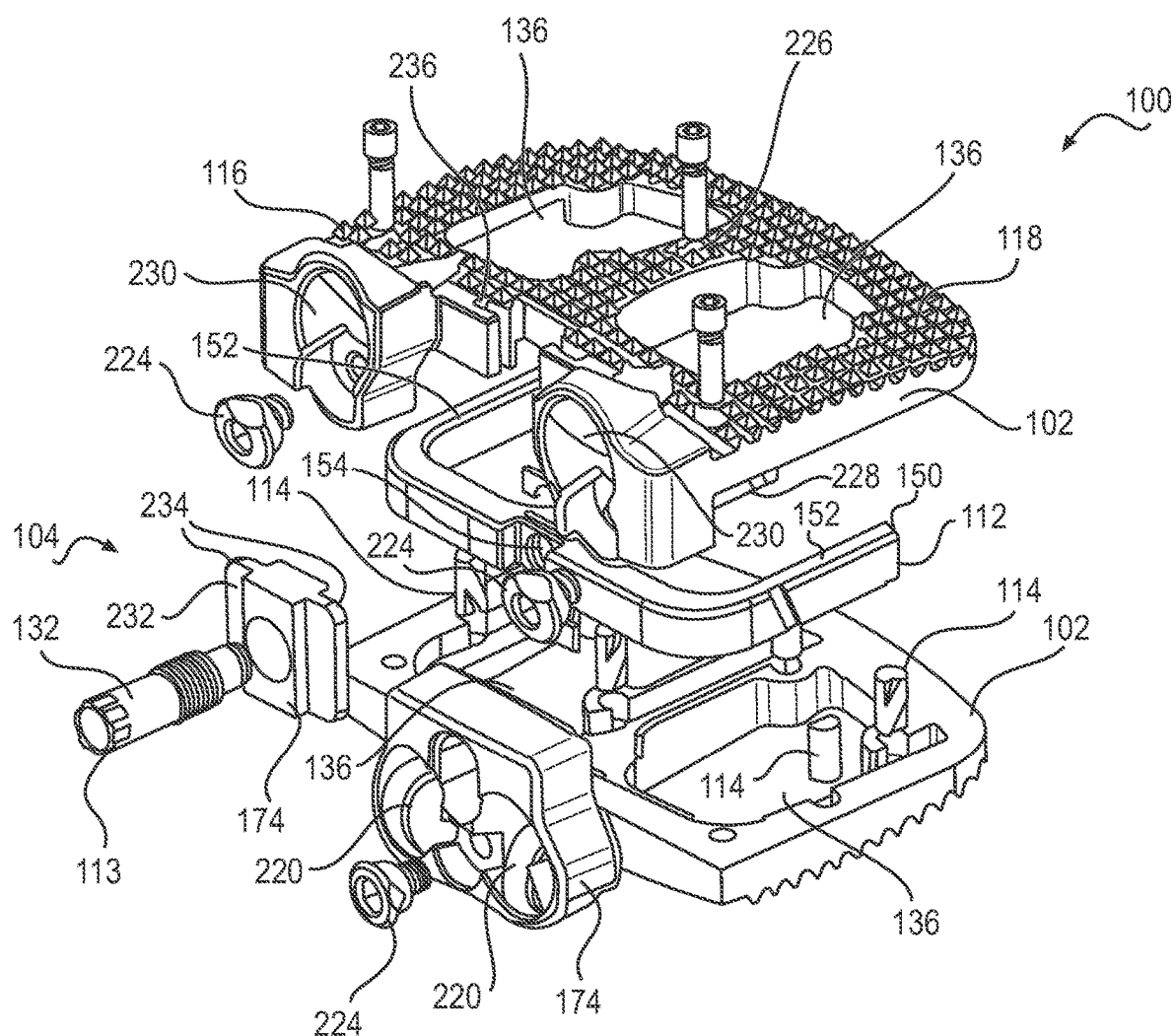
FIG. 21 is an exploded view of a spacer in accordance with example embodiments.
Figure 22:
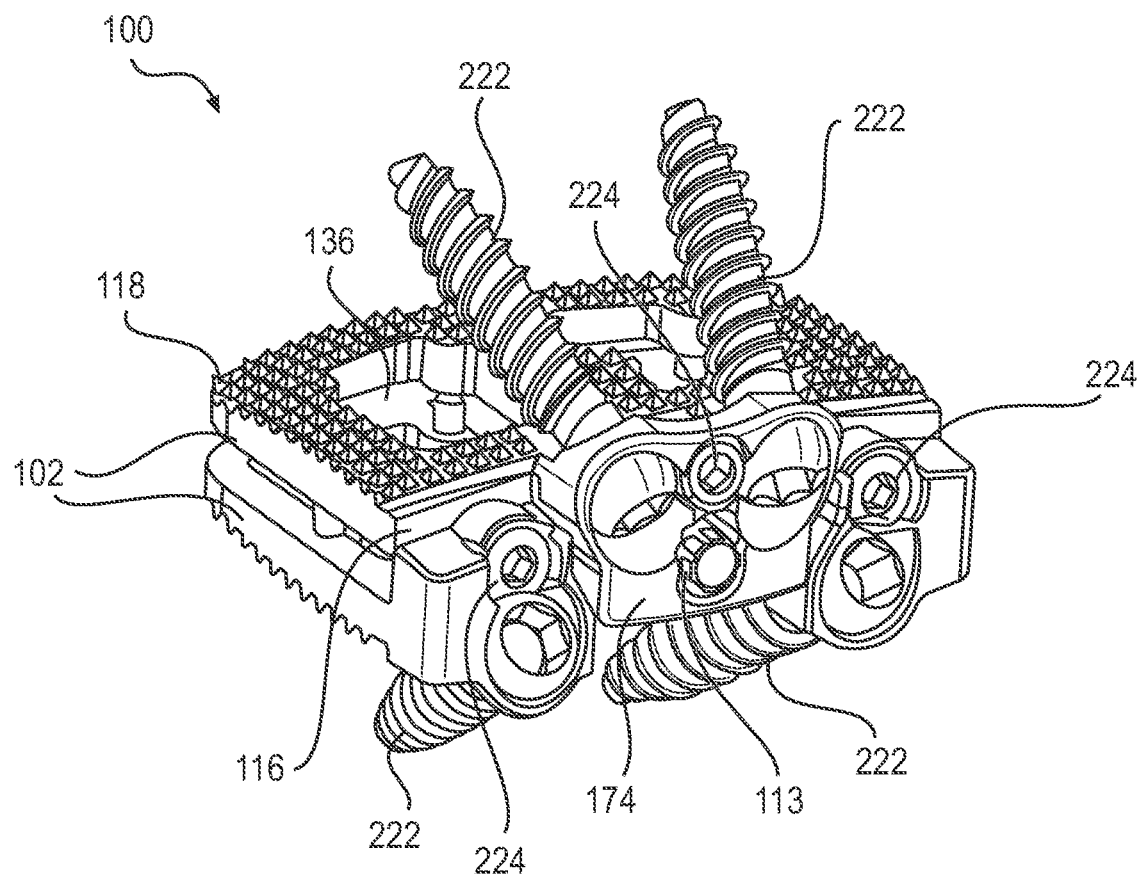
FIG. 22 illustrates a spacer in accordance with example embodiments.
Figure 23:
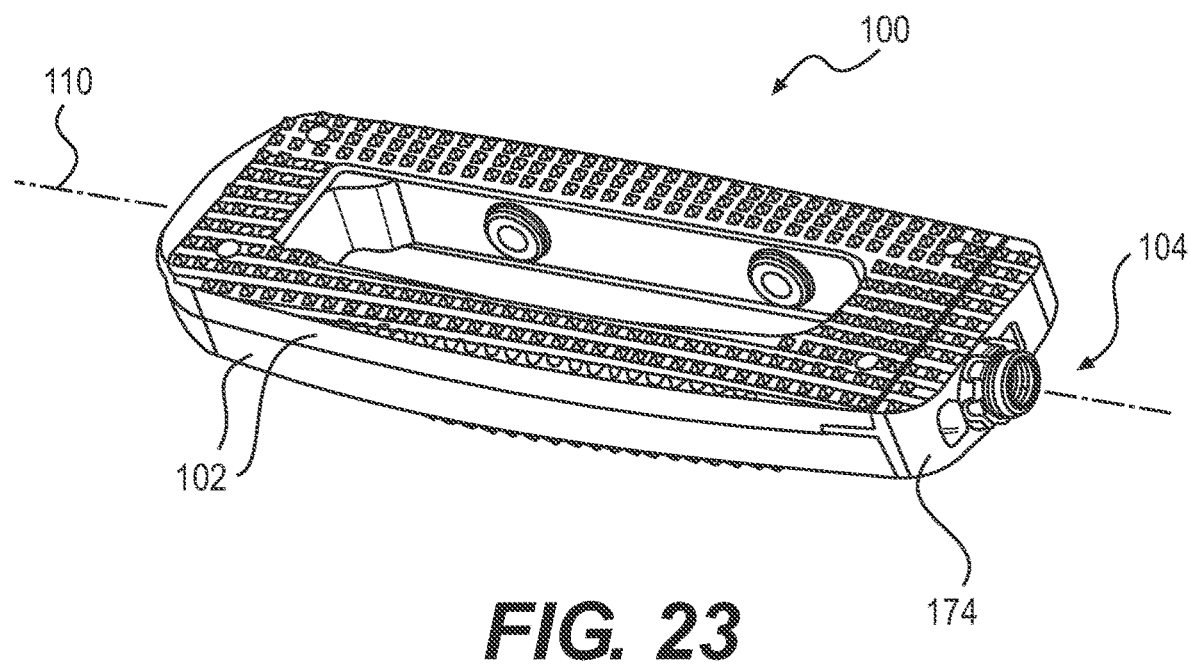
FIG. 23 is a perspective view of a spacer in a collapsed position in accordance with example embodiments.
Figure 24:
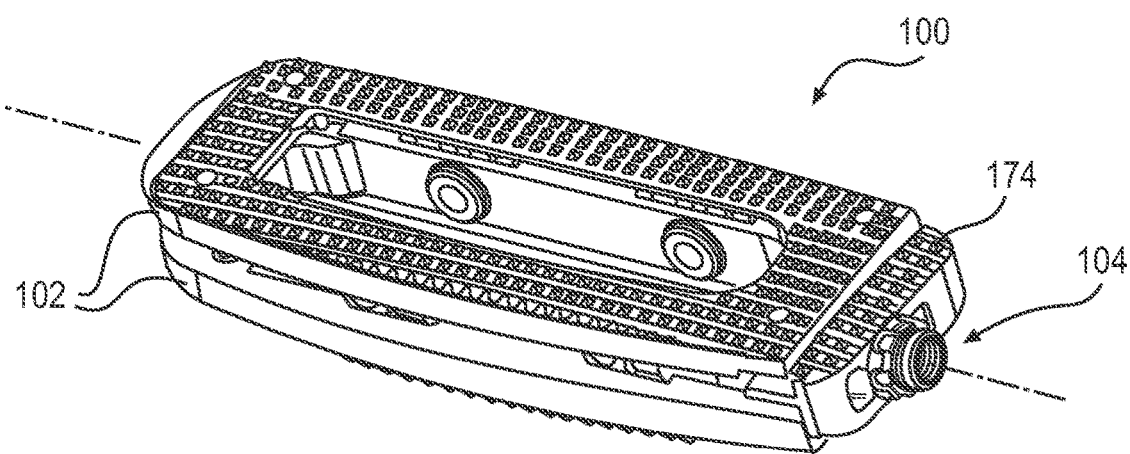
FIG. 24 is a perspective view of a spacer in an expanded position in accordance with example embodiments.
Figure 25:
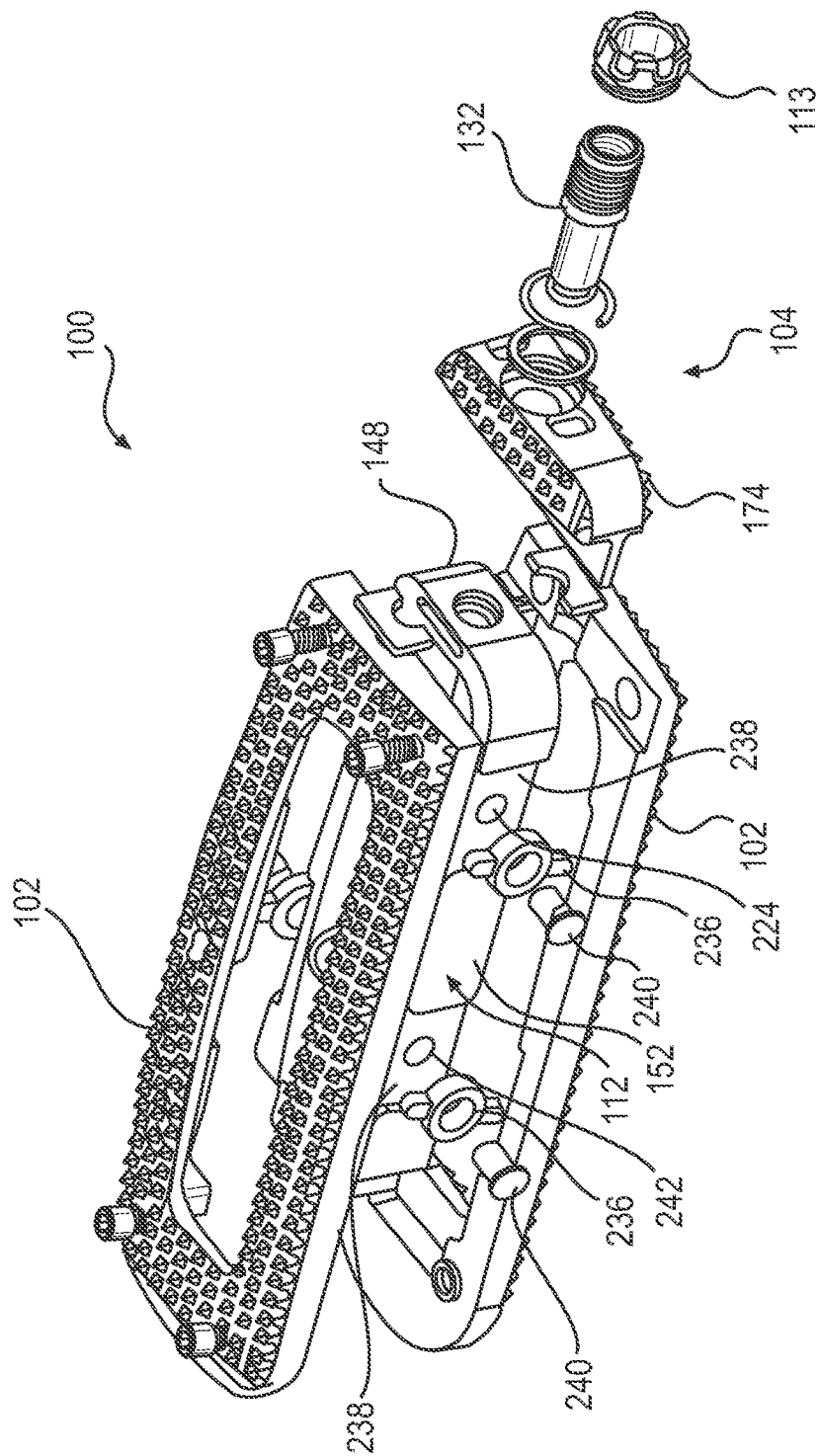
FIG. 25 is an exploded view of a spacer in accordance with example embodiments.
Figure 26:
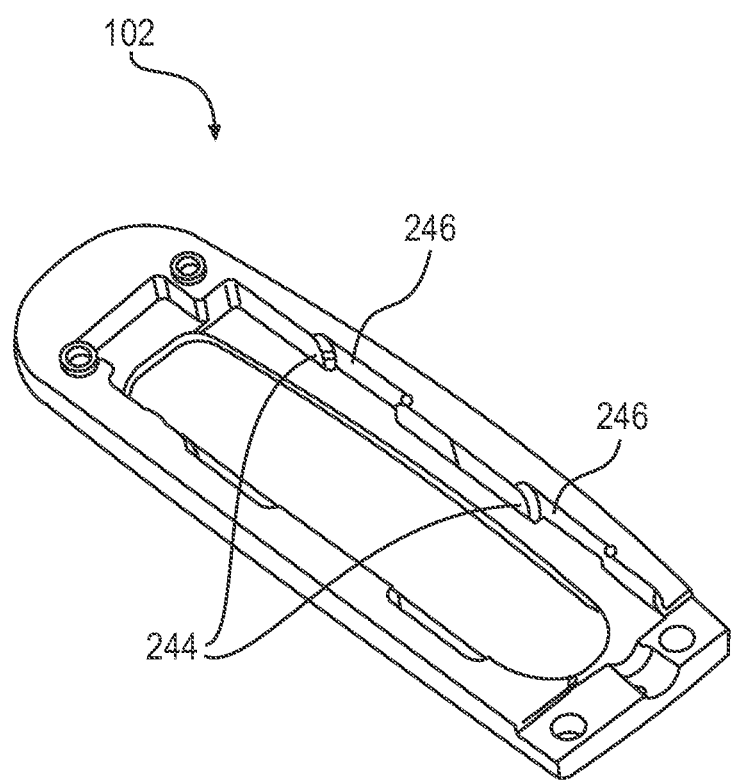
FIG. 26 illustrates an endplate of a spacer in accordance example embodiments.
Figure 27:
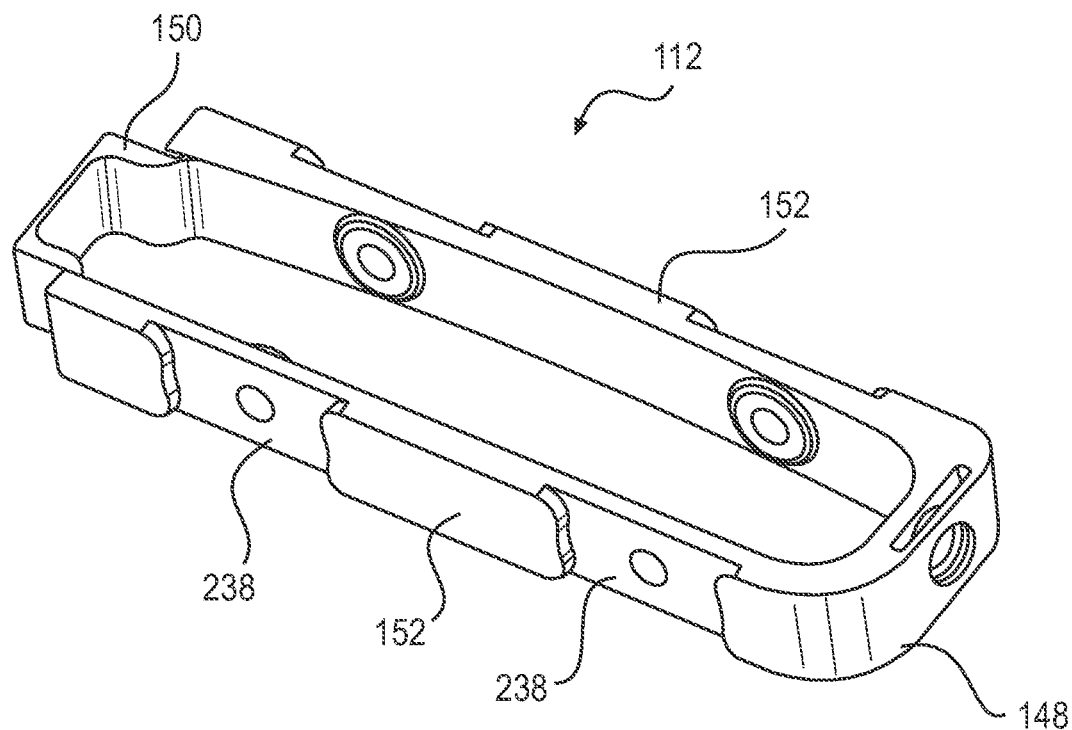
FIG. 27 illustrates a cam frame of a spacer in accordance with example embodiments.

FIGS. 12 and 13 illustrate spacer insertion device 202 in accordance with embodiments of the present invention. Spacer insertion device 202 may be used to engage spacer 100 during its insertion into a patient and also to actuate spacer 100 after its insertion. As illustrated, spacer insertion device 202 may comprise a handle portion 204 and an implant holder portion 206. Spacer insertion device 202 may further comprise an inner shaft 208 and an outer shaft 210. As best seen on FIG. 13, inner shaft 208 may include a threaded end 212 onto which the spacer 100 may be threaded. For example, threaded end 212 may thread into a threaded opening 214 of drive screw 132 (e.g., shown on FIG. 3). Implant holder portion 206 may also include ears 216 (or other projections) that engage corresponding insertion tool engagements 134 (e.g., shown on FIG. 3) of front plate 174. Implant holder portion 206 may also include drive nut interface 218 (best seen on FIG. 13) that engages drive nut 113 to cause rotation of drive nut 113.

Referring now to FIGS. 14-18, in an alternative embodiment, in which like numbers correspond to like elements in other embodiments herein, a spacer 100 is illustrated. As illustrated, the spacer 100 may comprise endplates 102 and actuation subassembly 104. Actuation subassembly 104 may comprise drive nut 113, drive screw 132, and cam frame 112. Spacer 100 may further comprise front plate 174. As previously described, cam frame 112 may engage cam pins 114 driving them into endplates 102, forcing the endplates 102 apart. Embodiments of spacer 100, and the various components thereof, shown on FIGS. 14-18 may be similar in function and operation to spacer 100 shown on FIGS. 1-11 except that plate body 176 of front plate 174 may further include bone fastener receiving holes 220. Bone fastener receiving holes 220 may extend through front plate 174 at an angle with respect to spacer longitudinal axis 110. Bone fastener receiving holes 220 may be sized and configured to receive a bone fastener 222, best seen on FIG. 18. Bone fastener 222 may be any suitable fastener for securing front plate 174 to adjacent tissue, such as vertebral bodies. Examples of suitable bone fasteners 222 may include, without limitation, bone screws and bone shanks. As best seen on FIG. 18, front plate 174 may further include a blocking screw 224. Blocking screws 224 may be rotated to block bone fasteners 222 and retain bone fasteners 222 in bone fastener receiving holes 220. While spacer 100 shown on FIGS. 14-18 may be implanted using a variety of approaches, spacer 100 may be particularly suitable for a lateral approach.

Referring now to FIGS. 19-22, in an alternative embodiment, in which like numbers correspond to like elements in other embodiments herein, a spacer 100 is illustrated. As illustrated, the spacer 100 may comprise endplates 102 and actuation subassembly 104. Actuation subassembly 104 may comprise drive nut 113, drive screw 132, and cam frame 112. Spacer 100 may further comprise front plate 174. Front plate 174 may comprise bone fastener receiving holes 220 for receiving bone fasteners 222. Blocking screw 224 may be disposed in front plate 174 and may be rotated to retain bone fasteners 222 in bone fastener receiving holes 220. As previously described, cam frame 112 may engage cam pins 114 driving them into endplates 102, forcing the endplates 102 apart. While spacer 100 shown on FIGS. 19-22 may be implanted using a variety of approaches, spacer 100 may be particularly suitable for an anterior or anterolateral approach.

Embodiments of spacer 100, and its various components, shown on FIGS. 19-22 may be similar in function and operation to embodiments of spacer 100 shown on FIGS. 19-22, except that spacer 100 may have a different configuration. By way of example, instead of one through opening 136 in endplates 102, each endplate 102 may comprise a pair of through openings 136. In addition, endplates 102 may also comprise a central extension 226 that extends from plate proximal end 116 to plate distal end 118. Additionally, cam frame 112 (best seen on FIG. 21) may be open at one end, for example, the distal frame end 150, which may be opposite opening 154. Moreover, a central frame extension 228 may extend from proximal frame end 148 between lateral frame sides 152. With respect to endplates 102, one of the endplates 102 (e.g., the uppermost endplate) may comprise front sockets 230 for receiving bone fasteners 222. Blocks screws 224 may be disposed in front sockets 230 for retaining bone fasteners 222 therein. Additionally, middle plate 232 may be disposed behind front plate 134, as best seen on FIG. 21. Middle plate 232 may receive drive screw 132 and have wings 234 that fit in corresponding grooves of endplates 102. While drive nut 113 has previously been described as being a separate components, embodiments may include a drive nut 113 integral to, or otherwise formed with, drive screw 132, as best seen on FIG. 21.

Referring now to FIGS. 23-30, in an alternative embodiment, in which like numbers correspond to like elements in other embodiments herein, a spacer 100 is illustrated. As illustrated, the spacer 100 may comprise endplates 102 and actuation subassembly 104. Actuation subassembly 104 may comprise drive nut 113, drive screw 132, and cam frame 112. Spacer 100 may further comprise front plate 174. Cam frame 112 may comprise cams 236 coupled thereto that engage endplates 102, force the endplates 102 apart, as cam frame 112 is translated. While spacer 100 shown on FIGS. 23-30 may be implanted using a variety of approaches, spacer 100 may be particularly suitable for a lateral approach. Embodiments of spacer 100, and the various components thereof, shown on FIGS. 23-30 may be similar in function and operation to spacer 100 shown on FIGS. 1-11 except that cam frame 112 may comprise cams 236 instead of cam slots 160.

With reference to FIGS. 25 and 27-30, embodiments of cam frame 112 will now be described in more detail. As previously described, cam frame 112 may comprise proximal frame end 148 and distal frame end 150, which are both coupled by lateral frame sides 152. In some embodiments, cam clearance slots 238 may be formed on lateral frame sides 152. Cam clearance slots 238 may be sized and configured to allow for unobstructed rotation of cams 236, for example. Cams 236 may be coupled to cam frame 112. As illustrated, cams 236 may be coupled in cam clearance slots 238. Cam pins 240 may pivotably retain cams 236 in connection with cam frame 112. In the illustrated embodiment, cam pins 240 may be unitary, but cam pins 240 may alternatively be provided in segments. Cams 236 may rotate about cam pins 240. Cam pins 240 may be received in pin holes 242, for example, in cam clearance slots 238. With additional reference to FIGS. 26 and 27, cams 236 may engage drive surfaces 244 in cam cutouts 246 of endplates 102. Cam cutouts 246 may be formed in lateral sides 124 of endplates 102.

Figure 28:
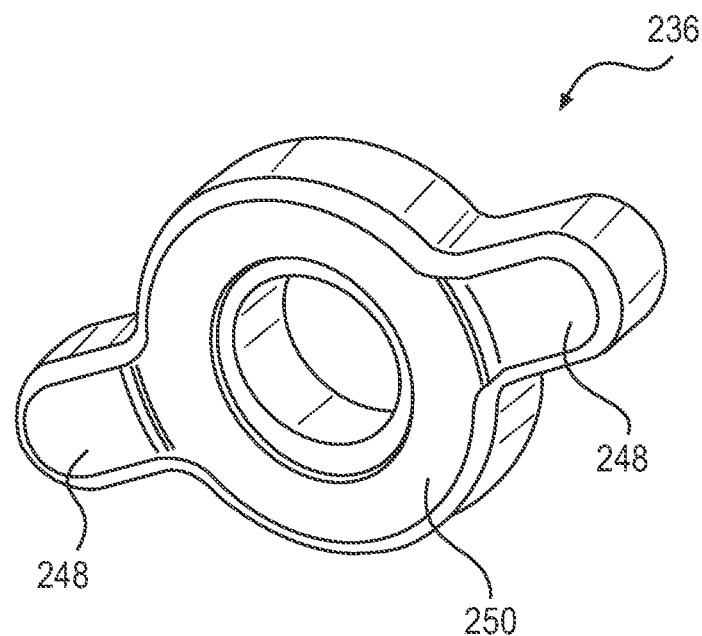
FIG. 28 illustrates a cam of a spacer in accordance with example embodiments.
Figure 29:
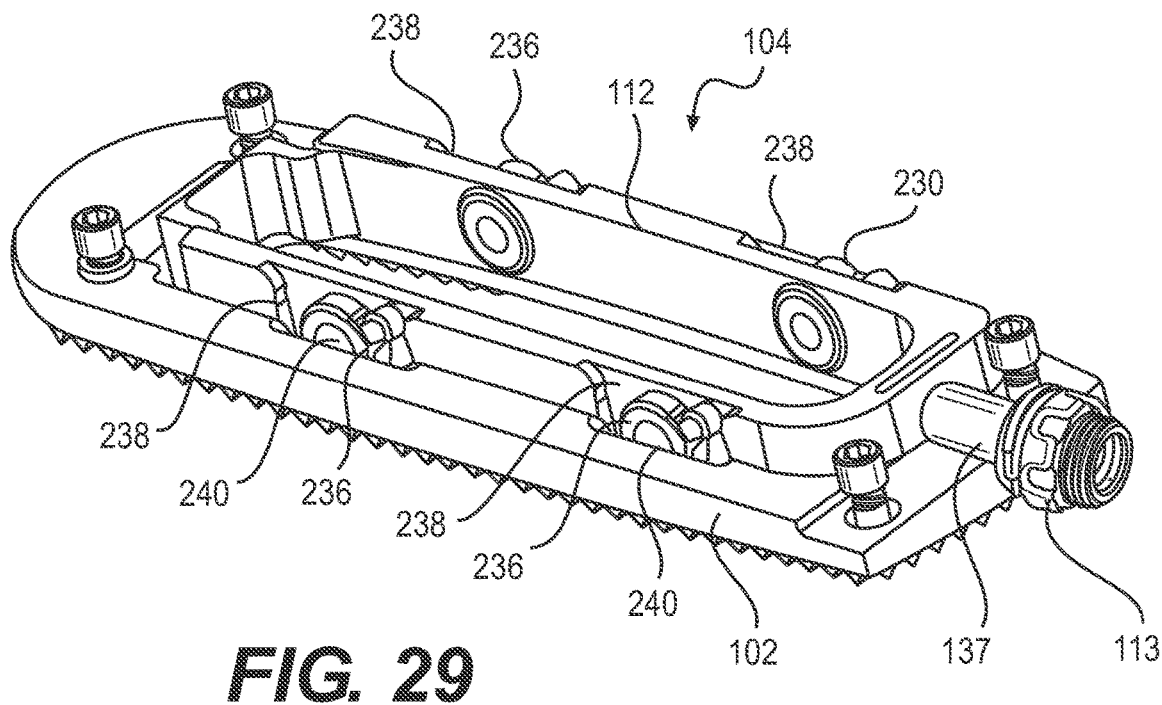
FIGS. 29 and 30 illustrate an actuation subassembly positioned with an endplate in accordance with example embodiments.
Figure 30:
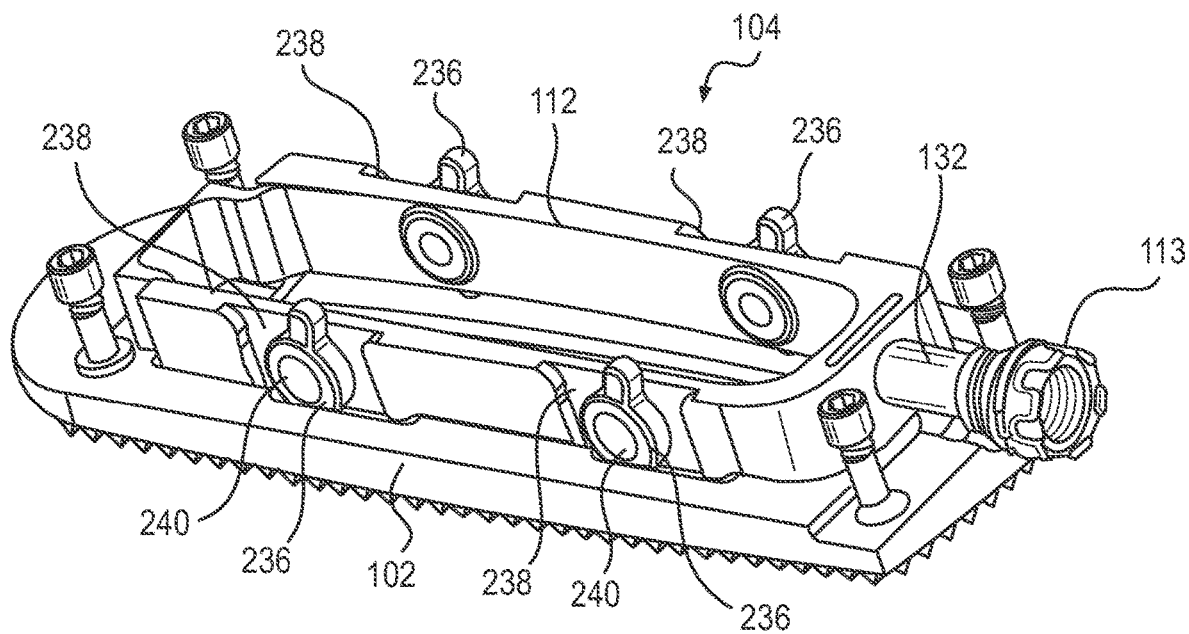
Figure 31:
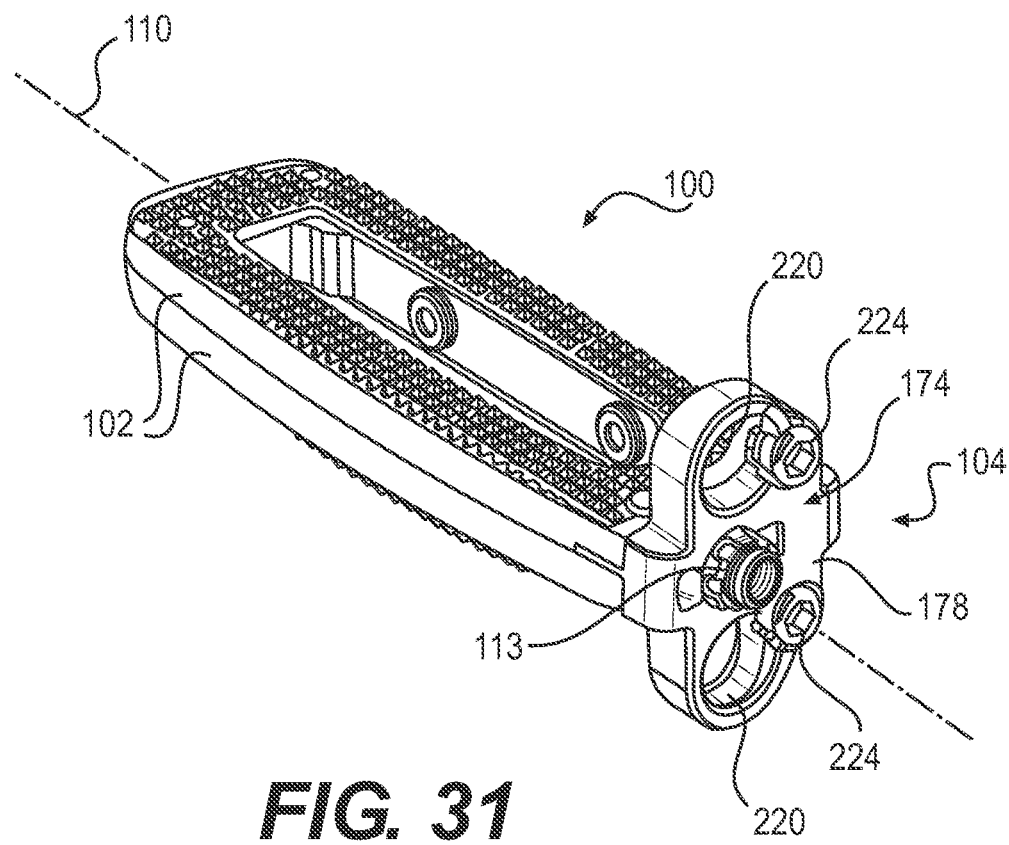
FIG. 31 is a perspective view of a spacer in a collapsed position in accordance with example embodiments.
Figure 32:
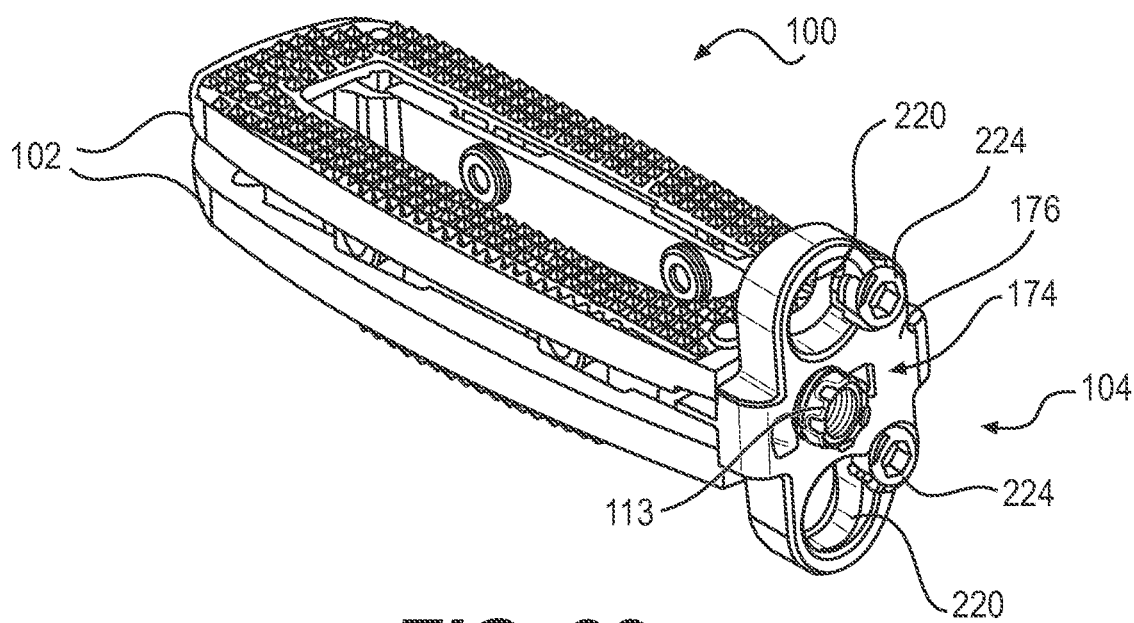
FIG. 32 is a perspective view of a spacer in an expanded position in accordance with example embodiments.
Figure 33:
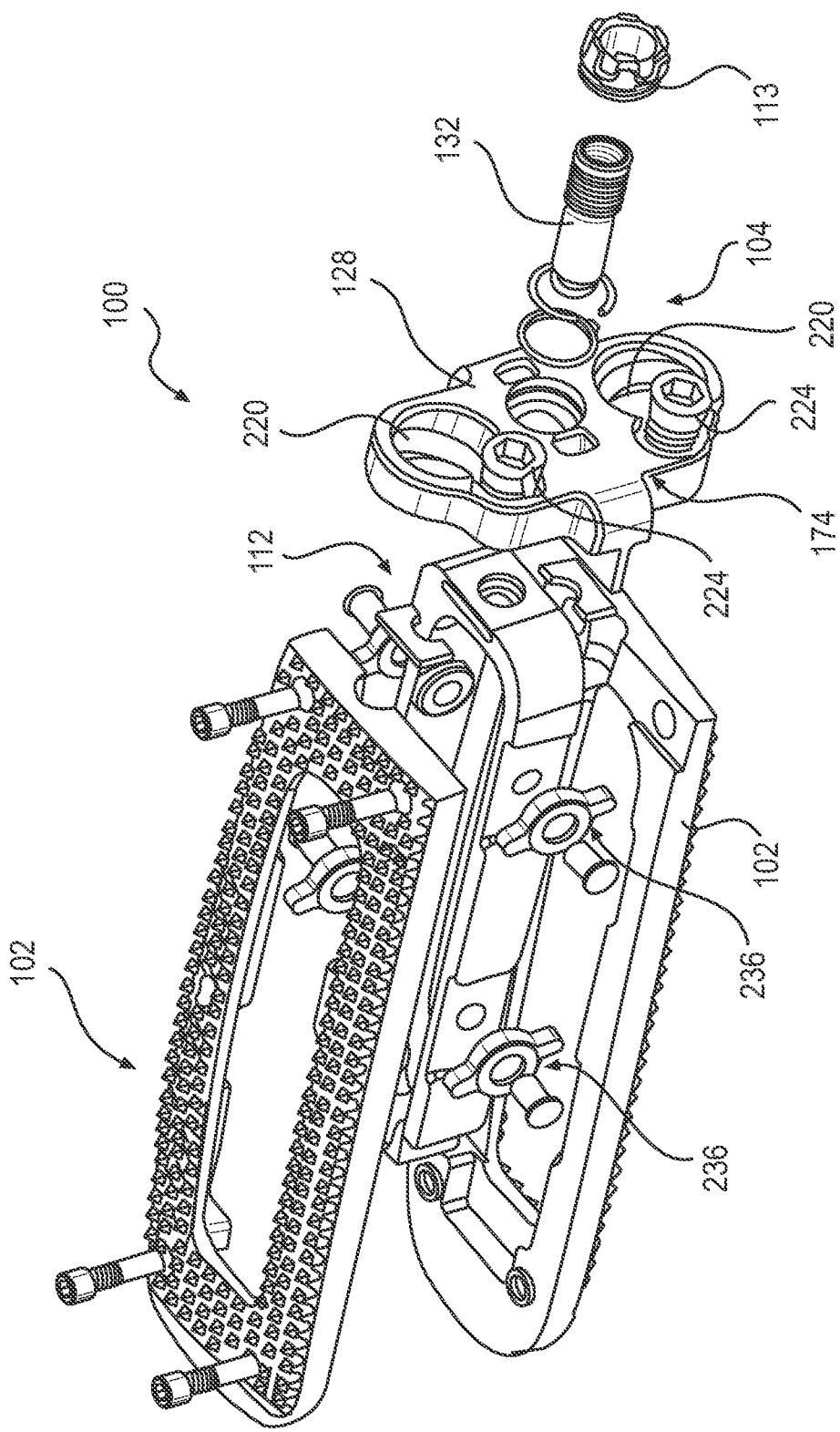
FIG. 33 is an exploded view of a spacer in accordance with example embodiments.
Figure 34:
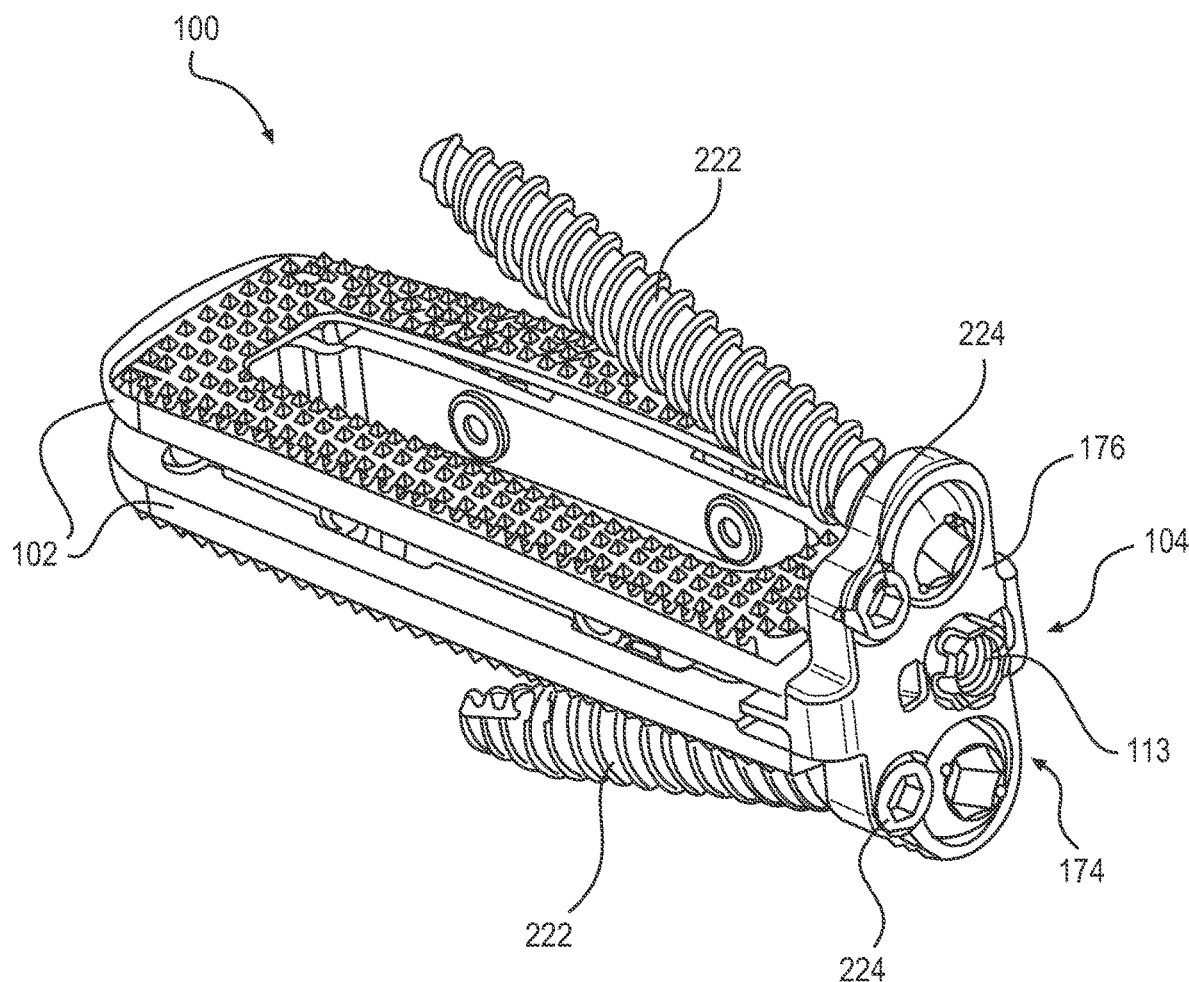
FIG. 34 illustrates a spacer in accordance with example embodiments.

As best on FIG. 28, a cam 236 may comprise a body portion 250, which may be generally circular in shape, but other shaped body portions 250, such as square, elliptical, etc., may also be suitable. Cam arms 248 may extend from body portion 250. Cam arms 248 may engage endplates 102. For example, cam arms 248 may engage drive surfaces 244 of endplates 102. The cams 236 may operate to change the direction of the linear movement of cam frame 112. For example, movement of the cam frame 112 along the spacer longitudinal axis 110 may be changed to movement of endplates 102 in a direction generally transverse to spacer longitudinal axis 110. As the cam frame 112 is moved, for example, along the spacer longitudinal axis 110, the cams 236 may engage drive surfaces 244 of endplates 102. As best seen on FIG. 26, drive surfaces 244 may be sloped in some embodiments. Cam 236 may rotate as cam frame 112 is moved with cam arms 248 pushing endplates 102 relatively apart such that a height of spacer 100 may be increased. Cams 236 may be arranged so that expansion may be achieved with advancement or withdrawal of cam frame 112 with movement of the cam frame 112 in the opposite direction causing the cams 236 to engage endplates 102 driving them to a collapsed positon.

Referring now to FIGS. 31-34, in an alternative embodiment, in which like numbers correspond to like elements in other embodiments herein, a spacer 100 is illustrated. As illustrated, the spacer 100 may comprise endplates 102 and actuation subassembly 104. Actuation subassembly 104 may comprise drive nut 113, drive screw 132, and cam frame 112. Spacer 100 may further comprise front plate 174. As previously described, cam frame 112 may comprise cams 236 that endplates 102 to drive them outward forcing expansion of spacer 100. Embodiments of spacer 100, and the various components thereof, shown on FIGS. 31-37 may be similar in function and operation to spacer 100 shown on FIGS. 23-30 except that plate body 176 of front plate 174 may further include bone fastener receiving holes 220. Bone fastener receiving holes 220 may extend through front plate 174 at an angle with respect to spacer longitudinal axis 110. Bone fastener receiving holes 220 may be sized and configured to receive a bone fastener 222, best seen on FIG. 18. Bone fastener 222 may be any suitable fastener for securing front plate 174 to adjacent tissue, such as vertebral bodies. Examples of suitable bone fasteners 222 may include, without limitation, bone screws and bone shanks. As best seen on FIG. 18, front plate 174 may further include a blocking screw 224. Blocking screws 224 may be rotated to block bone fasteners 222 and retain bone fasteners 222 in bone fastener receiving holes 220. While spacer 100 shown on FIGS. 31-34 may be implanted using a variety of approaches, spacer 100 may be particularly suitable for a lateral approach.

In some embodiments, spacer 100 may be fabricated using any biocompatible materials known or hereinafter discovered, having sufficient strength, flexibility, resiliency, and durability for the patient, and for the term during which the device is to be implanted. Examples include but are not limited to metal, such as, for example titanium and chromium alloys; stainless steel, polymers, including for example, PEEK or high molecular weight polyethylene (HMWPE); and ceramics. There are many other biocompatible materials which may be used, including other plastics and metals, as well as fabrication using living or preserved tissue, including autograft, allograft, and xenograft material. Portions or all of the spacer 100 may be radiopaque or radiolucent, or materials having such properties may be added or incorporated into the spacer 100 to improve imaging of the device during and after implantation. Any surface or component of a spacer 100 may be coated with or impregnated with therapeutic agents, including bone growth, healing, antimicrobial, or drug materials, which may be released at a therapeutic rate, using methods known to those skilled in the art.

In some embodiments, spacer 100 may be formed using titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Alternatively, part or all of spacers 100 may be formed with a polymer, for example ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of the disclosed spacers 100. For example, polymeric portions can be formed with PEEK-OPTIMA, which is radiolucent, whereby bony ingrowth may be observed. Other polymeric materials with suitable flexibility, durability, and biocompatibility may also be used.

In accordance with present embodiments, spacer 100 may be provided in various sizes to best fit the anatomy of the patient. Components of matching or divergent sizes may be assembled during the implantation procedure by a medical practitioner as best meets the therapeutic needs of the patient, the assembly inserted within the body using an insertion tool. In some embodiments, spacer 100 may also be provided with an overall angular geometry, for example an angular mating disposition of endplates, to provide for a natural lordosis, or a corrective lordosis, for example of from 0° to 12° for a cervical application, although much different values may be advantageous for other joints. Lordotic angles may also be formed by shaping one or both endplates to have relatively non-coplanar surfaces.

In some embodiments, a single spacer 100 may be used, to provide stabilization for a weakened joint or joint portion. Alternatively, a combination of two, three, or more of any of spacer 100 may be used, at a single joint level, or in multiple joints. Moreover, implants of the disclosure may be combined with other stabilizing means.

In some embodiments, a spacer 100 may be fabricated using material that biodegrades in the body during a therapeutically advantageous time interval, for example after sufficient bone ingrowth has taken place. Further, implants of the disclosure are advantageously provided with smooth and or rounded exterior surfaces, which reduce a potential for deleterious mechanical effects on neighboring tissues.

In some embodiments, a spacer 100 may be provided to be support adjacent vertebrae during flexion/extension, lateral bending, and axial rotation. In one embodiment, spacer 100 is indicated for spinal arthroplasty in treating skeletally mature patients with degenerative disc disease, primary or recurrent disc herniation, spinal stenosis, or spondylosis in the lumbosacral spine (LI-SI). The surgery to implant spacer 100 may be performed through an Anterior, Anterolateral, Posterolateral, Lateral, or any other approach.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Although the present invention and its advantages have been described in detail, it should be understood that various changes, substitutions and alterations may be made herein without departing from the spirit and scope of the invention as defined by the appended claims

The invention claimed is:

1. A spacer for separating bones of a joint, the spacer comprising:
   a first endplate configured to engage a first bone of the joint;
   a second endplate configured to engage a second bone of the joint; and
   an actuation subassembly comprising a drive nut, a drive screw coupled to the drive nut, and a frame coupled to the drive screw, wherein the frame is disposed between the first endplate and the second endplate, wherein the frame comprises a proximal end, a distal end, and lateral sides, and the frame comprise slots formed in the lateral sides of the frame and pins engage the slots, wherein rotation of the drive nut translates the frame, the frame engages the pins to selectively engage at least one of the first endplate or the second endplate.

2. The spacer of claim 1, wherein the spacer is moveable from a collapsed position to an expanded position, wherein, in the expanded position, the spacer has a height that is greater than a height in the collapsed position.

3. The spacer of claim 1, wherein the pins each comprise an elongated body portion and a ridge, wherein the ridge is at an angle with respect to the elongated body portion.

4. The spacer of claim 3, wherein the ridge of each of the pins engages a corresponding one of the slots.

5. The spacer of claim 1, wherein the drive screw comprises a threaded portion that threadingly engages a through bore of the drive nut.

6. The spacer of claim 1, wherein one end of the drive screw is retained in an opening in the proximal frame end, and another end of the drive screw is threadingly coupled to a through bore of drive nut.

7. The spacer of claim 1, wherein frame is open at the distal end.

8. The spacer of claim 1, at least one retention slot is formed in proximal frame end, wherein the at least one retention slot intersects an opening in the proximal frame end, and wherein one or more screw retention plates are positioned in the at least one retention slot to retain the drive screw in the opening.

9. The spacer of claim 1, further comprising a front plate, wherein the front plate comprise a plate body and an extension, wherein the plate body comprises bone fastener receiving holes configured to receive bone fasteners, and wherein the extension extends between the first endplate and the second endplate, the drive screw extending through the front plate.

10. The spacer of claim 1, wherein the first endplate further comprises front sockets configured to receive bone fasteners.

11. The spacer of claim 1, wherein the pins are pivotably secured in slots formed on the lateral frame sides.

12. A spacer for separating bones of a joint, the spacer comprising:
   a first endplate configured to engage a first bone of the joint;
   a second endplate configured to engage a second bone of the joint;
   an actuation subassembly comprising:
      a drive nut comprising a head portion and an extension from the head portion, wherein the extension is secured in a cutout formed by the first endplate and the second endplate;
      a drive screw comprising a threaded end that is threadingly coupled to a through bore of the drive nut;
      a frame comprising a proximal frame end, a distal frame end, and lateral sides, wherein slots are formed in the lateral frame sides, wherein the slots are at an angle with respect to a longitudinal axis of the spacer, wherein the drive screw is retained in an opening in the proximal frame end; and
      a plurality of pins that engage the slots and engage at least one of the first endplate and/or the second endplate.

* * * * *